(12) United States Patent
Su et al.

(10) Patent No.: US 10,704,088 B2
(45) Date of Patent: Jul. 7, 2020

(54) MASSIVELY PARALLEL INTEGRATED CIRCUIT-BASED DNA SYNTHESIS DEVICES, SYSTEMS, AND METHODS

(71) Applicant: Intel Corporation, Santa Clara, CA (US)

(72) Inventors: Xing Su, Menlo Park, CA (US); Grace Credo, San Mateo, CA (US)

(73) Assignee: Intel Corporation, Santa Clara, CA (US)

( * ) Notice: Subject to any disclaimer, the term of this patent is extended or adjusted under 35 U.S.C. 154(b) by 17 days.

(21) Appl. No.: 15/929,030

(22) Filed: Jun. 29, 2018

(65) Prior Publication Data

US 2019/0040458 A1 Feb. 7, 2019

(51) Int. Cl.
*C12Q 1/6844* (2018.01)
*B01J 19/00* (2006.01)
*B01L 3/00* (2006.01)
*C07H 21/04* (2006.01)

(52) U.S. Cl.
CPC ........ *C12Q 1/6844* (2013.01); *B01J 19/0046* (2013.01); *B01L 3/502753* (2013.01); *B01L 3/502784* (2013.01); *B01J 2219/00317* (2013.01); *B01J 2219/00387* (2013.01); *B01J 2219/00511* (2013.01); *B01J 2219/00596* (2013.01); *B01J 2219/00653* (2013.01); *B01J 2219/00689* (2013.01); *B01J 2219/00693* (2013.01); *B01J 2219/00722* (2013.01); *B01L 2200/025* (2013.01); *C07H 21/04* (2013.01)

(58) Field of Classification Search
CPC .. C12Q 1/6844; B01L 3/502753; C07H 21/04
See application file for complete search history.

(56) References Cited

U.S. PATENT DOCUMENTS

| | | | | |
|---|---|---|---|---|
| 8,603,803 B2* | 12/2013 | Wang | ................... | G01N 27/226 205/122 |
| 8,709,788 B2* | 4/2014 | El Gamal | ......... | B01L 3/502715 356/246 |
| 9,216,414 B2* | 12/2015 | Chu | ..................... | B01J 19/0046 |
| 9,981,239 B2* | 5/2018 | Banyai | ............... | C12N 15/1093 |
| 2006/0275927 A1* | 12/2006 | Dubin | .................. | B01J 19/0046 438/1 |
| 2016/0186166 A1* | 6/2016 | Poehmerer | .............. | B03C 5/026 205/420 |

* cited by examiner

Primary Examiner — Narayan K Bhat
(74) Attorney, Agent, or Firm — Thorpe North & Western, LLP

(57) ABSTRACT

DNA synthesis devices, systems, and methods are disclosed. An apparatus can include a synthesizer chip having an array of reaction units in a predetermined pattern, each reaction unit including a reaction surface and a reaction electrode of an IC array of reaction electrodes, and a synthesizer chip controller coupled to the IC array of reaction electrodes configured to address each reaction electrode individually. The apparatus can also include a reagent delivery chip positionable above the synthesizer chip, comprising an array of reagent delivery units arranged in the predetermined pattern, each reagent delivery unit including a reagent electrode of an IC array of reagent electrodes and each reagent delivery unit configured to receive and deliver a droplet of reagent fluid having a volume of 1 picoliter or less, and a reagent delivery chip controller coupled to the IC array of reagent electrodes configured to address each reagent electrode individually.

18 Claims, 11 Drawing Sheets

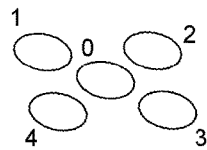 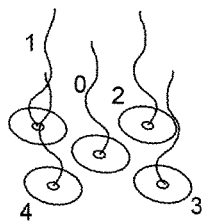 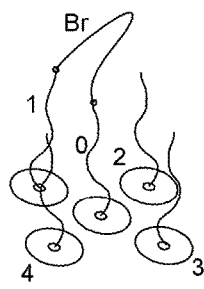 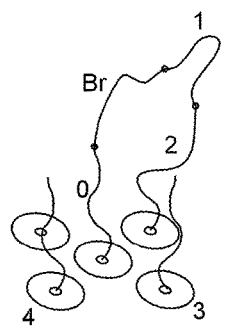
FIG. 9A    FIG. 9B    FIG. 9C    FIG. 9D
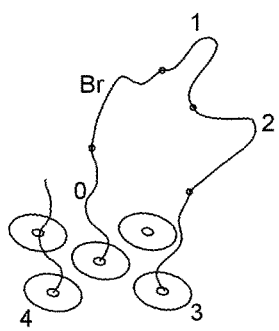 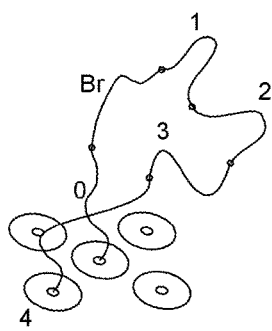 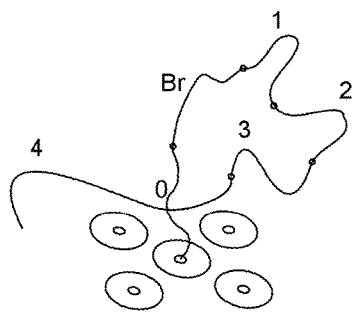
FIG. 9E    FIG. 9F    FIG. 9G
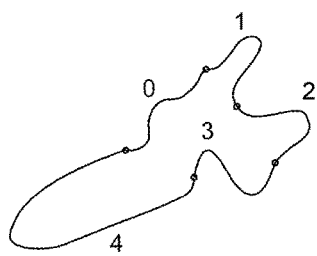
FIG. 9H

MASSIVELY PARALLEL INTEGRATED CIRCUIT-BASED DNA SYNTHESIS DEVICES, SYSTEMS, AND METHODS

BACKGROUND

The synthesis of polymeric molecules of nucleic acids such as deoxyribonucleic acid (DNA) and ribonucleic acid (RNA) can be performed for a variety of genetic and non-genetic purposes. DNA, for example, is a linear molecule of nucleotide (nt) base subunits that encodes the genetic instructions necessary for the creation, development, and reproduction of all known biological organisms. These genetic instructions are encoded in the sequences of the nucleotide subunits (nucleotides) in DNA molecules, which are generally comprised of two complimentary polynucleotide strands that are wound around each other to form a double helix. A nucleotide is made up of one of four nucleobases, cytosine (C), guanine (G), adenine (A), or thymine (T), a deoxyribose sugar, and a phosphate group. The nucleotides are joined together in a linear DNA strand by covalent bonds between the sugar of one nucleotide and the phosphate group of the next to create a sugar-phosphate backbone. The complimentary nature of the sequences of two DNA strands in a double helix comes from base pairing rules between nucleotides that are based on hydrogen bonding, such that A pairs with T and C pairs with G. In this manner, complimentary DNA strands wind together to form stable double helix structures while noncomplementary DNA strands do not. A single-stranded DNA can anneal (hybridize) to another single-stranded DNA or a portion of itself to form a double-stranded DNA (dsDNA) helix. DNA strands anneal or hybridize following the base-pairing rule, and thus each DNA strand has a nucleotide sequence that is complimentary to the nucleotide sequence of the annealed DNA strand.

BRIEF DESCRIPTION OF THE DRAWINGS

FIG. 9A shows an illustration of a collection of physically aggregated reaction surfaces in accordance with an example embodiment;

FIG. 9B shows an illustration of a collection of physically aggregated reaction surfaces each synthesizing a single-stranded DNA segment in accordance with an example embodiment;

FIG. 9C shows an illustration of a collection of physically aggregated reaction surfaces, a plurality of DNA segments, and a bridge DNA in accordance with an example embodiment;

FIG. 9D shows an illustration of a collection of physically aggregated reaction surfaces, a plurality of DNA segments, and a bridge DNA in accordance with an example embodiment;

FIG. 9E shows an illustration of a collection of physically aggregated reaction surfaces, a plurality of DNA segments, and a bridge DNA in accordance with an example embodiment;

FIG. 9F shows an illustration of a collection of physically aggregated reaction surfaces, a plurality of DNA segments, and a bridge DNA in accordance with an example embodiment;

FIG. 9G shows an illustration of a collection of physically aggregated reaction surfaces, a plurality of DNA segments, and a bridge DNA in accordance with an example embodiment;

FIG. 9H shows an illustration of a collection of a cyclized DNA oligonucleotide comprised of a plurality of DNA segments and a linker DNA segment in accordance with an example embodiment;

DESCRIPTION OF EMBODIMENTS

Figure 1A:
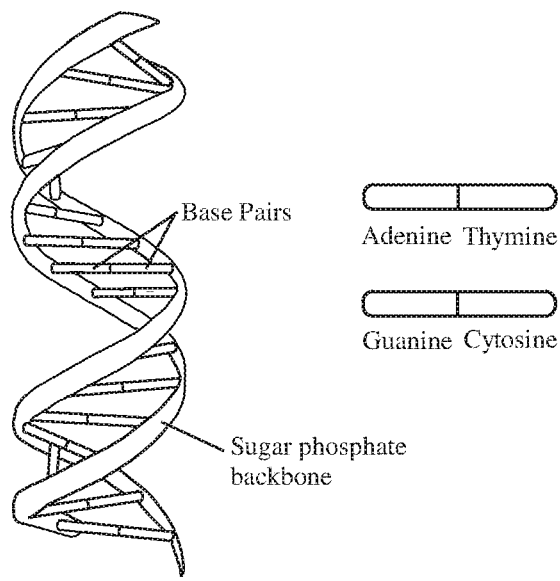
FIG. 1A shows an illustration of a segment of a double-stranded DNA helix.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals appearing in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other methods, components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device which is more likely to have write errors to it than other regions in the same memory device. A number of factors can cause such increased risk, including location, fabrication process, number of program pulses applied to the region, etc.

An initial overview of embodiments is provided below, and specific embodiments are then described in further detail. This initial summary is intended to aid readers in understanding the disclosure more quickly, and is not intended to identify key or essential technological features, nor is it intended to limit the scope of the claimed subject matter.

Figure 1B:
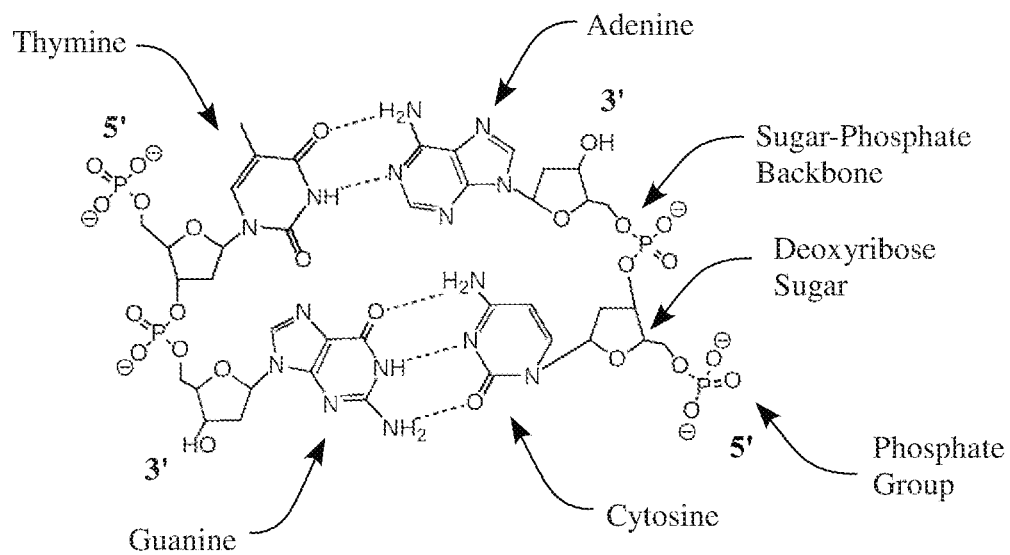
FIG. 1B shows an illustration of base pairing between nucleotides in a double-stranded DNA helix.

The synthesis of polymeric molecules of nucleic acids such as deoxyribonucleic acid (DNA) and ribonucleic acid (RNA) can be performed for a variety of genetic and non-genetic purposes. DNA, for example, is a linear molecule of nucleotide base subunits that encodes the genetic instructions necessary for the creation, development, and reproduction of all known biological organisms. These genetic instructions are encoded in the sequences of the nucleotide subunits (nucleotides) in DNA molecules. As is shown in FIG. 1A, most DNA includes two complimentary polynucleotide strands that are wound around each other to form a double helix, which is also known as double-stranded DNA (dsDNA). As is shown in FIG. 1B, each nucleotide is made up of one of four nucleobases, cytosine (C), guanine (G), adenine (A), or thymine (T), a deoxyribose sugar, and a phosphate group. The nucleotides are joined together in a linear DNA strand by covalent bonds between the sugar of one nucleotide and the phosphate group of the next to create a sugar-phosphate backbone (see FIG. 1B). The complimentary nature of the sequences of two DNA strands in a double helix comes from base pairing rules between nucleotides that are based on hydrogen bonding, such that A pairs with T and C pairs with G. In this manner, complimentary DNA strands wind together to form stable double helix structures while noncomplementary DNA strands do not. A single-stranded DNA can anneal (hybridize) to another single-stranded DNA or a portion of itself to form a dsDNA helix. DNA strands anneal or hybridize following the base-pairing rule, and thus each DNA strand has a nucleotide sequence that is complimentary to the nucleotide sequence of the annealed DNA strand.

Each DNA strand molecule has a 5' end and a 3' end that is determined by the open position in the deoxyribose sugar, where typically a 5' end has an open phosphate group and a 3' end has an open hydroxyl group. In a dsDNA helix the direction of the nucleotide sequences of each strand are in an antiparallel orientation to one another, or in other words, a dsDNA helix includes one strand extending in the 5'-3' direction and the other strand extending in the 3'-5' direction. Biochemically, a DNA strand is always elongated (polymerized) in the 5'-3' direction. Chemically, a DNA strand can be elongated (polymerized) in either one of the two directions.

A single-stranded DNA molecule is about 1 nm in diameter and has a spacing of about 0.34 nm between each nucleotide base. Due to this small diameter and spacing, physical DNA is highly compressible, allowing vast amounts of information encoded in the sequence of the associated nucleotides. For example, the DNA in the largest human chromosome (chromosome 1) contains about 220 million nucleotide base pairs, but only has a linear length of 85 mm when straightened out.

DNA synthesis can include a variety of synthesis techniques that generally involve the sequential addition of nucleotides to a growing strand of DNA, where genetic or non-genetic information can be encoded in the sequence of nucleotides. Using traditional DNA synthesis systems, however, is a very expensive and time-consuming process, at least in part due to the limited throughput per reaction cycle wasting significant amounts of reagent, which greatly reduces the practical uses of synthesized DNA. The size of reaction wells (or reaction regions) in a DNA synthesis system correlate with the amount of reagent that is needed to sufficiently fill each reaction well, and any unused reagent is discarded as waste at the end of each synthesis cycle. Additionally, size of the reaction wells is negatively correlated with the number of reaction wells that can be present per unit surface area of support substrate, which thus limits the number of DNA molecules that can be sequenced per cycle. Reducing the size of the reaction wells can thus allow an increase in reaction wells per unit surface area of the support substrate, as well as reducing the amount of reagent used per DNA molecule per synthesis cycle. In other words, reducing the size of the reaction wells can greatly increase the throughput of a DNA synthesizer. As one caveat, however, is that smaller reaction wells utilize solution volumes that are sufficiently small such that fluid evaporation needs to be taken into account. These evaporative effects are generally negligible in larger volume reactions due to the greater solution volume in each reaction well. As the volume of the solution in each reaction well decreases, however, these evaporative effects can begin to have a negative impact on the synthesis reactions, or even halt them altogether. In other words, droplet/well sizes that are of sufficient size to significantly increase throughput have volumes that run the risk of solution evaporation before synthesis is complete. In this situation, the reaction wells would need to be refilled to finish the sequence cycle, thus causing a decrease in DNA synthesis throughput. As an additional issue, the movement of solution droplets to and from the reaction wells can be extremely challenging at very small volumes.

The presently disclosed technology provides a solution to these problems by providing a reaction substrate or chip having reaction wells of a sufficiently small size to allow massively parallel DNA synthesis. In addition, the presently disclosed technology provides a solution/reagent transfer element that can effectively transfer droplets of reagent/solution to and from the reaction chip in a manner that minimizes evaporation to an extent that DNA synthesis cycles can be completed before solution droplet evaporation can occur.

Figure 2A:
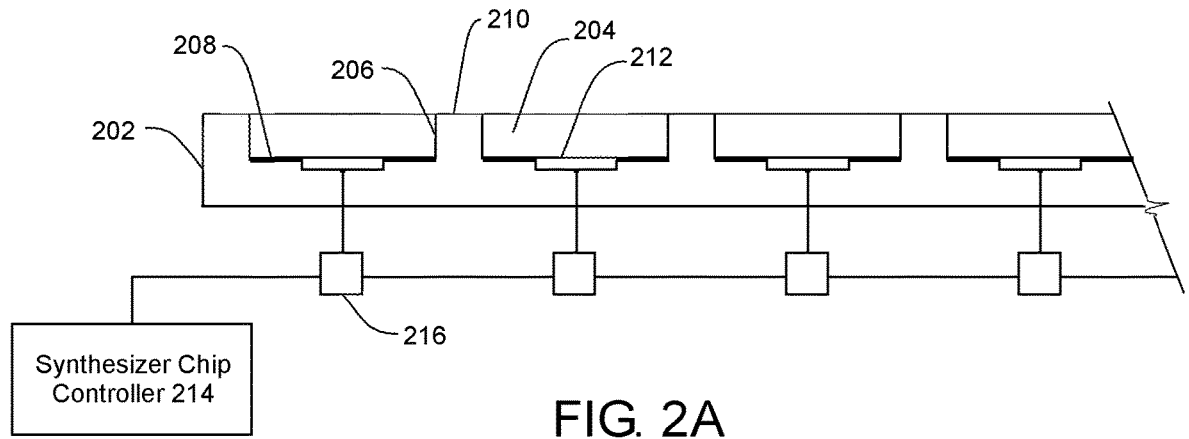
FIG. 2A shows a cross-section view of a series of reaction units in accordance with an example embodiment.

FIG. 2A shows an example of a reaction chip 202 having a plurality of reaction units 204 disposed thereon (or therein). Each reaction unit 204 includes a well sidewall 206 and a well bottom 208, which can also be referred to as a reaction surface. Fluidic isolation between the reaction units 204 can be accomplished by a number of techniques/structures such as, for example, a well barrier 210 that forms a physical barrier around each reaction unit 204, which in some cases can form the well sidewall 206. The well barrier 210 can be an extension of the reaction chip 202 as shown, or a separately-formed structure of either the same material as the reaction chip 202 or a different material from the reaction chip 202. In another example, reaction "well" regions of a hydrophilic material can be disposed across the surface of a reaction chip as a plurality of reaction surfaces that are each fluidically isolated from one another by a hydrophobic layer disposed therebetween. In yet another example, reaction units can be fluidically isolated by an atmospheric barrier. One technique for implementing such a barrier would be to form the plurality of reaction "wells" or reaction surfaces across the tops of a plurality of columns dispersed across the reaction chip, and sufficiently spaced to preclude the fluid from adjacent reaction units from coming into contact.

Each reaction unit 204 (or reaction surface, depending on the embodiment) additionally includes a reaction electrode 212 electrically coupleable to a DNA synthesizer controller 214. The DNA synthesizer controller 214 can selectively control each reaction electrode 212 via an associated reaction electrode switch 216. The reaction electrodes 212 can protrude from the surface or they can be recessed into the surface. The reaction electrode 212 can be designed to have sufficient surface area and geometry to hold or otherwise manipulate any desired volume of reagent fluid. In one nonlimiting example, an exposed electrode surface can be about 1 $\mu m^2$ or more. In another nonlimiting example, an exposed electrode surface can be <1 $\mu m^2$.

Figure 2B:
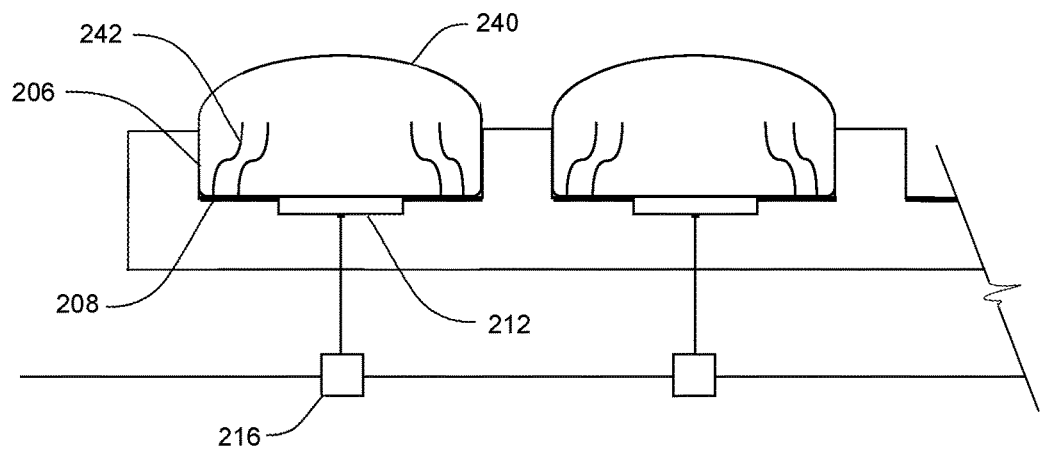
FIG. 2B shows a cross-section view of a series of reaction units in the process of synthesizing DNA in accordance with an example embodiment.

FIG. 2B illustrates an example of two reaction units 204 filled with a reagent fluid 240. A plurality of DNA strands 242 are shown coupled to the well bottom 208, which are undergoing DNA synthesis. As synthesis proceeds, the DNA strands 242 extend linearly in a direction from the well bottom 208. The well bottom 208 can include a hydrophilic coating to facilitate initiation of DNA strand synthesis, which in some cases can be non-conductive. Any hydrophilic coating capable of supporting DNA synthesis is contemplated, which in some examples can include oxides, such as silicon oxide, silicon nitride, aluminum oxide, iron oxide, or the like, organic polymers, such as polysaccharides, peptides, nucleic acids, or other synthetic polymers, and combinations thereof. It is additionally noted that, in some implementations, a hydrophilic layer can additionally be applied to the well sidewall 206 to allow DNA synthesis to proceed therefrom. The reaction electrodes 212 can be made from any conductive material that is compatible with DNA synthesis, nonlimiting examples of which can include metals such as gold, silver, platinum, aluminum, or the like, including alloys thereof. Conductive materials that are incompatible with DNA synthesis can also be used, provided the well electrode surfaces are isolated from the synthesis reactions by a material that is compatible with DNA synthesis.

Additionally, regions separating adjacent reaction units 204, such as well barrier 210 for example, can be hydrophobic or hydrophilic depending on the design of the reaction chip 202. In one example, such separation regions can be hydrophobic, by forming the separation region from hydrophobic materials or via a hydrophobic coating or chemical modification such as, for example, a fluoro-compound such as polytetrafluoroethylene or other perfluorocarbon compound, a small molecule HMDS (hexadimethylsilazane) coating, or the like. In other examples, surface texturing can be used to form a hydrophobic surface, such as physical or topographic modification methods that include material films that have such properties, including etched or otherwise fabricated 3D features on the surface that have been demonstrated to repel fluids.

While they can be of any size, in one example reaction units can have a diameter of less than 35 µm for a circular-shaped reaction unit. It is noted that the present disclosure is not limited to circular reaction units, and that those skilled in the art can readily convert between any shape of reaction unit and a circular reaction unit for comparison purposes. In some nonlimiting examples, reaction units can have a diameter of from 0.1 µm to 12 µm, from 0.1 µm to 10 µm, from 0.1 µm to 5 µm, or from 0.1 µm to 1 µm, or less. In another example, a reaction unit can be defined based on a volume of fluid that can be held therein having at least a concave fluid meniscus with sufficient fluid in the reaction unit to successfully perform a DNA synthesis reaction. The fluid volume is additionally considered to include any fluid volume forming a convex meniscus contained above the reaction unit. Accordingly, in one example a reaction unit can be of any size and shape that can receive, and successfully perform a DNA synthesis reaction with, a droplet of reactant fluid having a volume from 1 attoliter (aL) to 1 picoliter (pL), from 125 femtoliters (fL) to 16 attoliters, from 1 fL to 16 aL, or from 125 aL to 16 aL.

Given the small sizes of such droplets, the vapor pressure of the solvent can be adjusted to minimize evaporation. The typical solvent used in DNA synthesis is acetonitrile, which has a relatively high vapor pressure and can easily evaporate. To reduce its evaporation rate, acetonitrile or other high vapor pressure solvents such as dichloromethane can be mixed with low molecular weight polyethylene glycol (for example, H(OCH□CH□O)$_n$OH MW: 200 g/mol., 300 g/mol., 400 g/mol., etc.), glycerol, or any other additive to reduce the mole fraction of acetonitrile or other high vapor pressure solvent and thus lower the vapor pressure. Alternatively, other solvents or solvent mixtures with lower vapor pressures can be used. Potential lower vapor pressure solvents include propylene carbonate (PC), 2-methylglutaronitrile (MGN), 3-methoxyproprionitrile (3MP), a 1:1 mixture of MGN:3MP by volume, or an alternative mixture of MGN and 3MP that could span the range of 10:1 MGN:3MP to 1:10 MGN:3MP by volume. As is described further below, the liquid handling operations can be performed in a manner that minimizes evaporation, such as using sealed reaction media, performing fluid transfer in vapor-controlled chambers, or any other technique for limiting evaporation.

In order to perform DNA synthesis in such small volumes of solution, the present disclosure provides a fluid/reagent delivery system capable of addressing and fluidically interacting with any number of any pattern of reaction units across the entire surface of the reaction chip, from a single reaction unit to all of the reaction units simultaneously.

Furthermore, the delivery and removal of fluid droplets to and from the reaction units is noncontact transfer, meaning that the fluid system and the associated reaction unit are not in fluidic contact with one another during the fluid transfer. This can be accomplished using electrostatic charge to drive the fluid droplet back and forth between the reaction unit and the fluid transfer system. When opposing electrodes are oppositely charged with the reagent solution on the negatively charged electrode, for example, the negatively-charged reagent solution can be transferred electrostatically to the positively charged electrode. The electric field between the two electrodes can be highly confined due to the size of the electrode surfaces, which can allow precise delivery of charged fluid droplets between the two. The shape and surface characteristics of the reaction unit can be configured to further increase the precision of the delivery, for example by using hydrophobic surface coatings to direct fluid into the reaction unit. The amount of reagent delivered to the reaction electrode, for example, can be optimized through adjustments made to the strength and duration of the electric field, the distance between the electrodes, the dimensions of electrode surface, and the like.

Figure 3C:
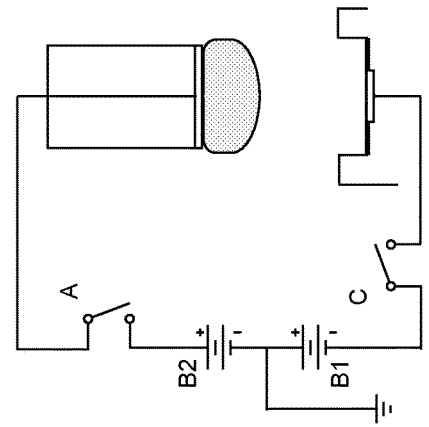
FIG. 3C shows a cross-section view of a reaction unit and a reagent delivery unit in accordance with an example embodiment.
Figure 3D:
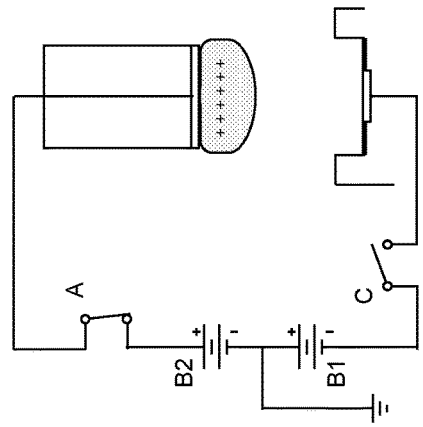
FIG. 3D shows a cross-section view of a reaction unit and a reagent delivery unit in accordance with an example embodiment.
Figure 3B:
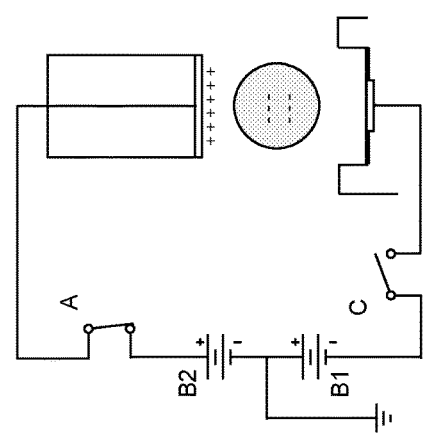
FIG. 3B shows a cross-section view of a reaction unit and a reagent delivery unit in accordance with an example embodiment.
Figure 3E:
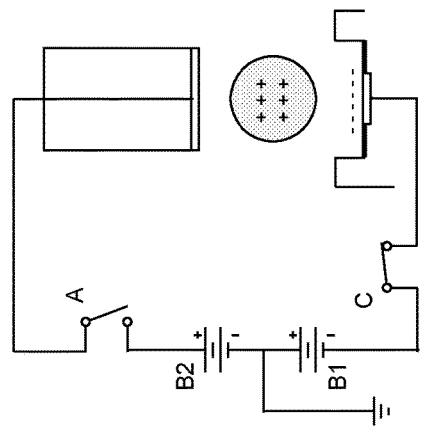
FIG. 3E shows a cross-section view of a reaction unit and a reagent delivery unit in accordance with an example embodiment.
Figure 3A:
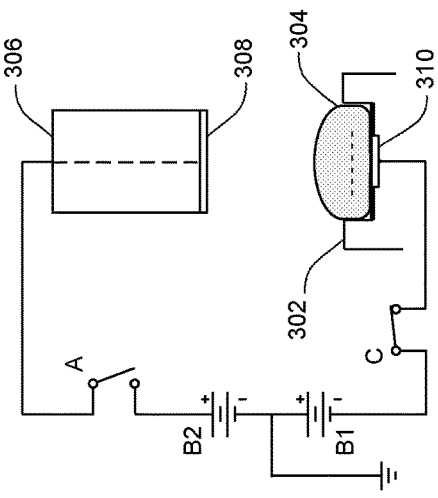
FIG. 3A shows a cross-section view of a reaction unit and a reagent delivery unit in accordance with an example embodiment.
Figure 3F:
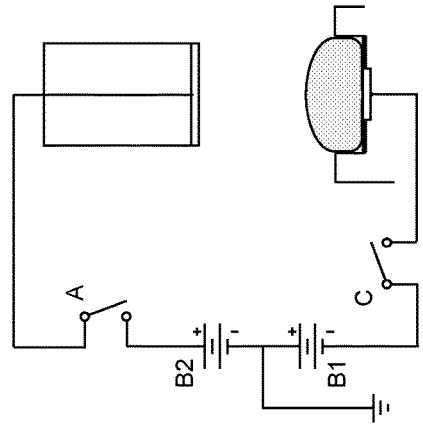
FIG. 3F shows a cross-section view of a reaction unit and a reagent delivery unit in accordance with an example embodiment.

As a more detailed example, FIGS. 3A-F show a contactless transfer utilizing electrostatic forces. FIG. 3A shows a single reaction unit containing a fluid droplet 304. A single reagent delivery unit 306 is shown positioned above and in alignment with the reaction unit 302, which includes a reagent electrode 308 facing the reaction electrode 310. The reaction electrode 310 and the reagent electrode 308 are each electrically coupleable to power sources B1 and B2 through switch C and switch A, respectively. As such, the state of the switches A and C controls electrostatic charge on each respective electrode. For FIG. 3A, the negative terminal of the power source B1 is coupled to the closed switch C, which introduces a negative charge into the fluid droplet 304 through the reaction electrode 310. When switch C is opened and switch A is closed, as shown in FIG. 3B, the negative charge is released from the reaction electrode 310 and the negatively-charged fluid droplet 304 is electrostatically attracted to the reagent electrode 308, where the negative charge on the fluid droplet 304 is discharged. Given its small volume, the fluid droplet 304 can be maintained on the reagent electrode 308 without having a charge. Delivery of the fluid droplet 304 from the reagent delivery unit 306 is shown in FIG. 3D, where switch A is closed to positively charge the reagent electrode 308, thus introducing a positive charge into the fluid droplet 304. Closing switch C negatively charges the reaction electrode 310, thus causing the positively charged fluid droplet 304 to be electrostatically transferred from the reagent electrode 308 to the negatively charged reaction electrode 310, where the fluid droplet 304 is discharged. It is noted that the positive and negative charging relationships can be reversed.

Figure 4A:
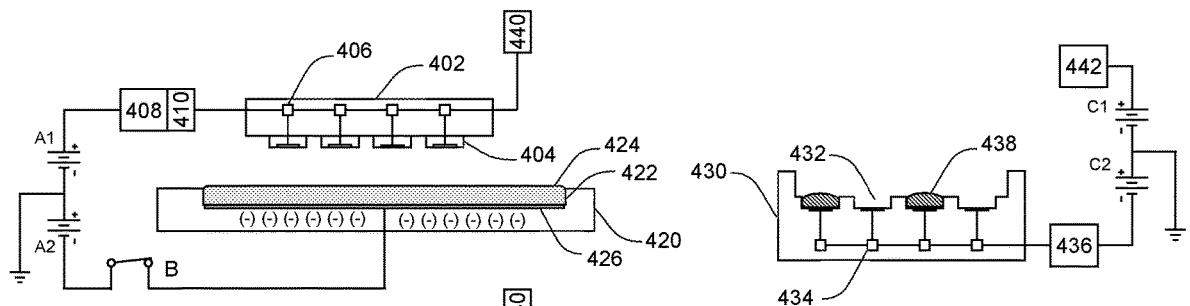
FIG. 4A shows a cross-section view of a reagent delivery chip above a reagent solution tray beside a synthesizer chip in accordance with an example embodiment.

In this manner, an array of reagent delivery units can be aligned with an array of reaction units to transfer fluid droplets discretely back and forth between the associated electrodes. Because each of the reaction unit/reagent delivery unit pairs can be individually addressed, a different DNA sequence can potentially be synthesized simultaneously in each reaction unit. One example is illustrated in FIG. 4A-E, which has been limited to four reaction units for clarity. FIG. 4A shows a reagent delivery chip 402 including an array of reagent delivery units 404 that is switchably controlled via an array of reagent electrode switches 406. The reagent electrode switch array 406 can be based on any type of power semiconductor device, semiconductor gate, switching element, or the like. In one nonlimiting example, the reagent electrode switches can be metal-oxide-semiconductor field-effect transistor (MOSFET) elements, including n-channel or p-channel type operating in either enhancement or depletion mode. In some cases, the reagent electrode switch array can be an array of MOSFET elements implemented as a complimentary MOSFET (CMOS) array. In other nonlimiting examples, the reagent electrode switches can be insulated-gate bipolar transistors (IGBTs), bipolar junction transistors (BJTs), or the like. The array of reagent electrode switches 406 can be managed by an upstream reagent electrode switch controller 408 through an upstream reagent controller interface 410, which can vary depending on the design of the reagent electrode switches, the complexity of the array, and the like.

FIG. 4A also shows a synthesizer chip 430 including a plurality of reaction units 432 in the form of reaction units into at least a portion of which reagent solution 424 is to be transferred by the array of reagent delivery units 404. The dark fluid 438 shown in some reaction units 432 represents a portion of the reaction units that have been filled with a reaction fluid from a prior fluid transfer 438. The synthesizer chip 430 further includes an IC array of reaction electrode switches 434 electrically coupled and corresponding to the plurality of reaction units 432. The IC array of reaction electrode switches 434 can be switchably controlled by a reaction electrode controller 436, which can independently activate any reaction electrode in the array by closing the reaction electrode switch 434 associated with that reaction electrode. For the design of FIG. 4A, closing any of the reaction electrode switches 434 will electrically couple the negative terminal of power source C2 to the reaction electrode associated with the closed reaction electrode switch, thus negatively charging that reaction electrode. As with the reagent electrode switch array, the array of reaction electrode switches 434 can be based on any type of power semiconductor device, semiconductor gate, switching element, or the like. In one nonlimiting example, the reaction electrode switches 434 can be MOSFET elements, including n-channel or p-channel type operating in either enhancement or depletion mode. In some cases, the reaction electrode switch array can be an array of MOSFET elements implemented as a CMOS array. In other nonlimiting examples, the reagent electrode switches can be insulated-gate bipolar transistors (IGBTs), bipolar junction transistors (BJTs), or the like.

To load at least a portion of the array of fluid delivery units 404 with a reagent solution, the reagent delivery chip 402 is positioned over a solution tray 420. The solution tray 420 has a recessed region 422 in which a reagent solution 424 is contained. A fluid tray electrode 426 is positioned along a bottom surface of the recessed region 422 in order to facilitate the electrostatic transfer of reagent solution 424 from the solution tray 420 to one or more reagent delivery units 404 of the reagent delivery chip 402. It is noted, that the fluid tray electrode 426 can be a single electrode as shown, or a plurality of fluid tray electrodes aligned with the array of reagent delivery units 404. A power source A2 is configured to electrically couple to the fluid tray electrode 426 through switch B. As such, for the example shown in FIG. 4A, closing switch B electrically couples the fluid tray electrode 426 to a negative terminal of the power source A2, which negatively charges the reagent solution 424.

Figure 4B:
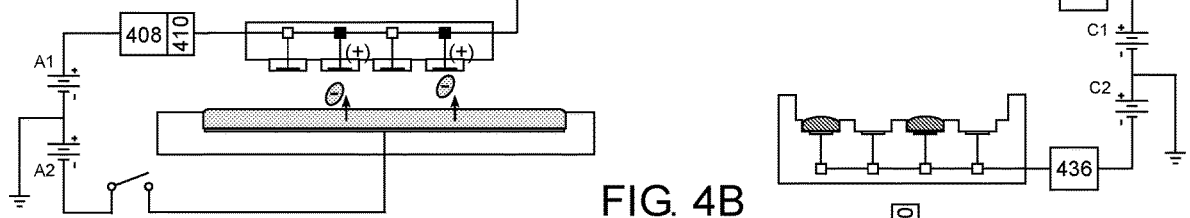
FIG. 4B shows a cross-section view of a reagent delivery chip above a reagent solution tray beside a synthesizer chip in accordance with an example embodiment.

Turning to FIG. 4B, it is noted that a portion of the reaction units 432 in the synthesizer chip 430 are filled with the prior fluid transfer 438, and such filled reaction units will be generally avoided in a subsequent fluid transfer, unless such filled reaction units are only partially full and additional reagent is needed, or a mixture of different reagent solutions is intended. Across the entire array of reaction units 432, different reaction units will receive different reagent solutions depending on which reagents are needed in each reaction unit to proceed with a given synthesis reaction cycle. Thus, a system includes multiple solution trays that each include a solution used in the DNA synthesis cycle, either with or without specific reagents. For example, solution trays can contain buffer solutions, wash solutions, nucleotide solutions, enzymatic solutions, and the like. In the example shown in FIG. 4B, the reaction units filled with fluid from the prior fluid transfer 438 may be filled with a different reactant solution due to a different chemistry being performed. To allow a plurality of different reactions to be performed simultaneously with different reagents, the array of fluid transfer units 404 delivers reagent solutions selectively to the reaction units 432 using those reagents, and then picks up a different reagent solution from a different solution tray to selectively deliver to other reaction units 432 that are using that different reagent solution. This can be accomplished by positioning the fluid delivery chip 402 over the solution tray 420 and activating only those reagent electrode switches 406 of fluid deliver units 404 that correspond to (i.e., deliver to) reaction units 432 needing the reagent solution 424 or other fluid contained by the solution tray 420. Reagent electrode switches 406 that have been closed are shown as black squares in FIG. 4B and the (+) denotes the corresponding positively charged reagent delivery units. Negatively charged reagent solution is thus electrostatically transported only to the reagent electrodes in the array that are positively charged.

Figure 4C:
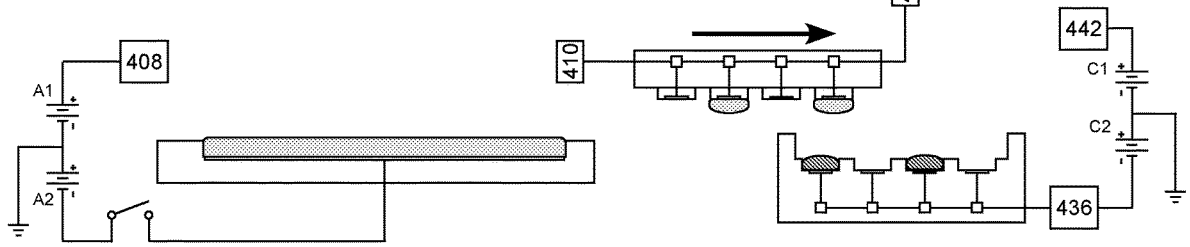
FIG. 4C shows a cross-section view of a reagent delivery chip moving from a position above a reagent solution tray to a position above a synthesizer chip in accordance with an example embodiment.

As is shown in FIG. 4C, the upstream solution controller 408 opens the closed reagent electrode switches and the droplets of reagent solution on the reagent delivery units 404 are discharged. The reagent delivery chip 402 is moved from its position above the solution tray 420 and is subsequently positioned over the synthesizer chip 430 described above. Once in position, the reagent delivery chip 402 can be moved downward to seal against the synthesizer chip 430 in order to minimize fluid loss, such as by evaporation. In some examples, the upstream solution controller 408 is uncoupled from the upstream solution controller interface 410 prior to or during the movement of the reagent delivery chip 402 from the position over the solution tray 420. In one example, the array of fluid control switches 406 can be communicatively coupled to a downstream solution controller 442 through a downstream fluid controller interface 440, which are coupled together during the move or thereafter. In other examples, the downstream fluid controller 442 and/or the upstream fluid controller 408 can be located on the reagent delivery chip 402, and thus move from the solution tray 420 to the synthesizer chip 430 along with the array of fluid control switches 406. In yet other examples, the upstream solution controller 408 and the downstream solution controller 442 can be the same solution controller.

Figure 4D:
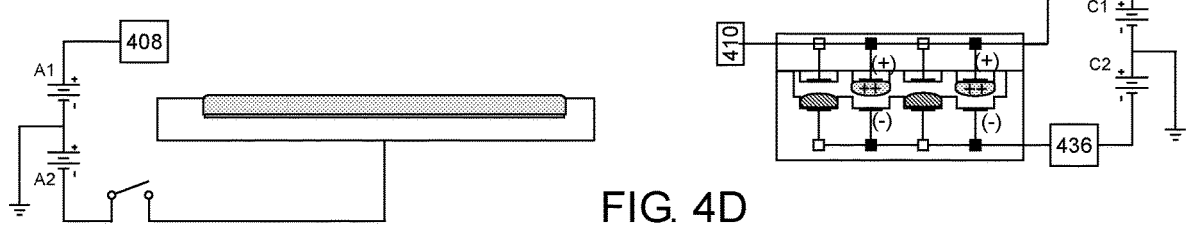
FIG. 4D shows a cross-section view of a reagent delivery chip sealed onto a synthesizer chip beside a reagent solution tray in accordance with an example embodiment.
Figure 4E:
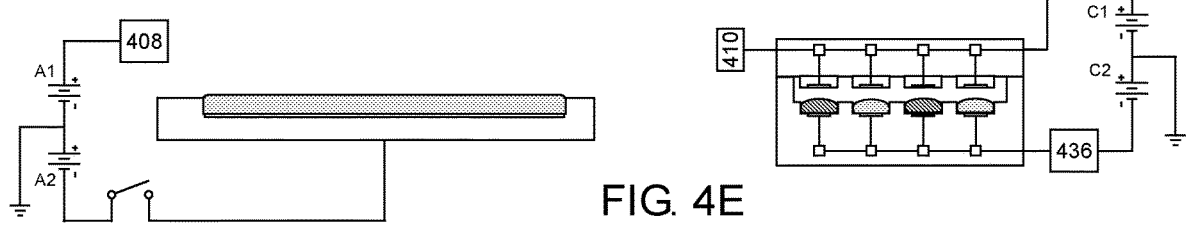
FIG. 4E shows a cross-section view of a reagent delivery chip sealed onto a synthesizer chip beside a reagent solution tray in accordance with an example embodiment.

FIG. 4D shows the reagent delivery chip 402 in an operating position and sealed onto the synthesizer chip 430. Once in position and sealed onto the synthesizer chip 430, the downstream fluid controller 442 closes or otherwise activates the reagent electrode switches 406 that are associated with fluid deliver units 404 having a solution associated therewith, thus charging the reagent solution associated with the activated electrodes. The reaction electrode controller 436 closes or otherwise activates the reaction electrode switches 434 in the reaction units 432 opposite the reagent delivery units 404 holding reagent solution to be delivered thereto. The downstream fluid controller opens or otherwise deactivates the reagent electrode switches 406 that are delivering reagent solution, thus discharging the associated reagent electrodes and causing the charged reagent solution to be transported from the reagent electrode to the reaction electrode in the opposite facing reaction units 404, as is shown in FIG. 4E.

In one example, the array of fluid control switches and/or the array of reaction electrode switches can be implemented as an integrated circuit (IC) chip. The specific IC can vary depending on numerous design choices, and any such design is considered to be within the present scope. In one example, however, the IC chip can be a CMOS chip. The IC can thus control the charging and discharging of the electrode surfaces selectively, as each electrode can be addressed individually, as described above.

Figure 5:
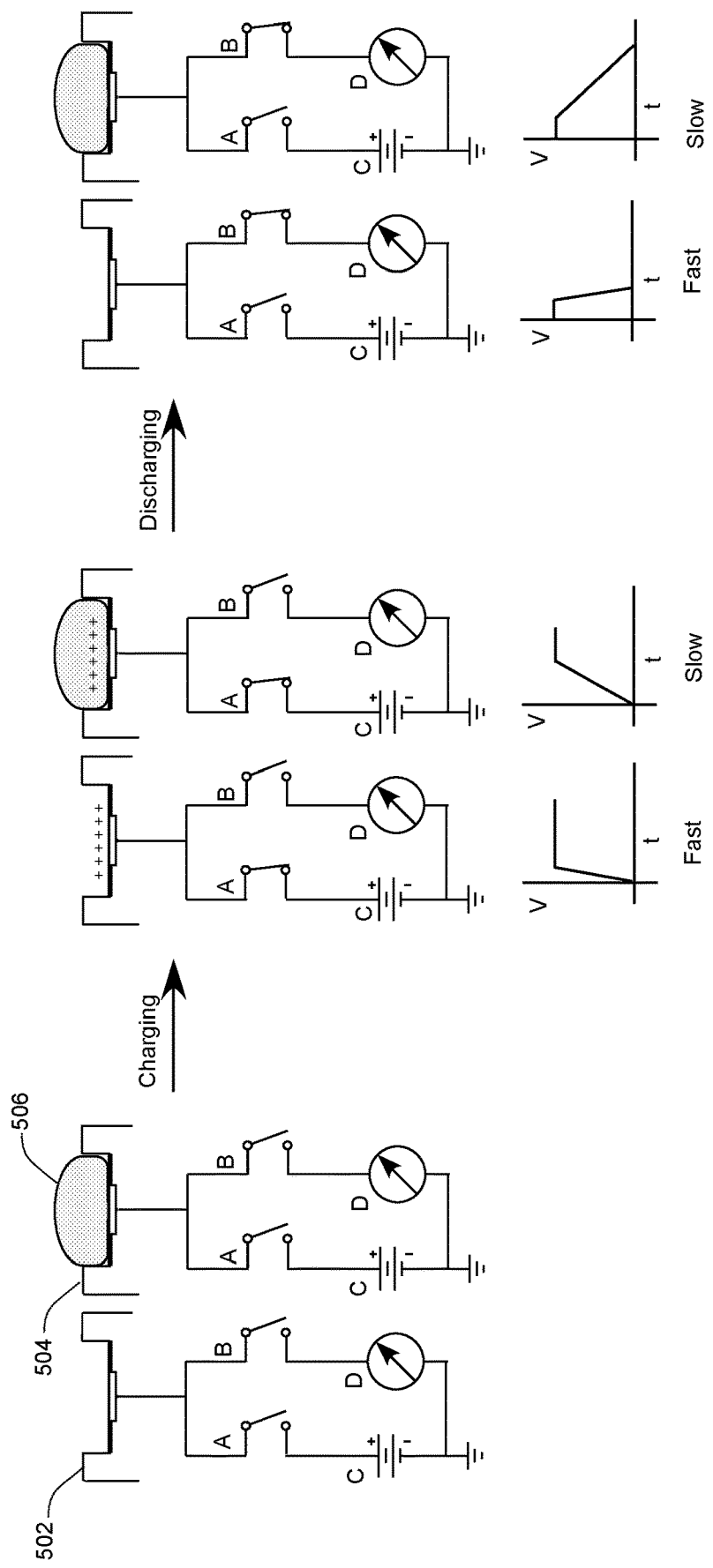
FIG. 5 shows a cross-section view of a pair of reaction units being charged and then discharged in accordance with an example embodiment.

Various quality control elements can be implemented to further increase DNA synthesis throughput by detecting error states that may occur during processing. Error states can include improperly filled or empty reaction units, spillage from one reaction unit to another, and the like. For example, FIG. 5 shows one technique for verifying that a reaction unit has been filled with a fluid by monitoring charge/discharge rates. Two reaction units are shown at the left side of FIG. 5, an empty reaction unit 502 (or well) and a full reaction unit 504 containing a fluid droplet 506. A circuit below each reaction unit includes switch A and switch B, a power source C, and a voltage sensor D. The middle section of FIG. 5 shows the electrodes in reaction units 502 and 504 being charged by closing switch A and leaving switch B open in each circuit to allow current to flow to the reaction electrodes. To discharge the reaction units 502 and 504, switch A is opened and switch B is closed in each circuit as is shown at the right in FIG. 5. This causes the reaction units to be discharged to ground, which is measured by the voltage sensor D. The rate and time course of charging and discharging can thus be monitored by the voltage sensor D and compared to identify any reaction units that were not properly filled. During discharge, the switch connecting to the source is off and the switch connecting to the ground is turned on. The discharge rate and amplitude can thus be monitored and compared. As can be seen from the Voltage/time graphs below each reaction unit example, there is a distinct difference between the charging/discharging profiles for empty vs full reaction units. For example, an empty reaction unit is charged rapidly because the limited number of free carriers in the electrode material rapidly fill with positive charge. A reaction unit filled with a fluid, on the other hand, has free charge carriers in the electrode material and in the fluid, which take longer to fill and come to a steady state. The discharging of the reaction units is similar, with the empty reaction unit discharging more quickly compared to the full reaction unit due to the fewer number of charge carriers.

Reaction unit filling can be monitored in various different ways. In one implementation, for example, reaction units are charged and then disconnected from power source C (i.e., both switch A and switch B are open) prior to reagent solution delivery to the reaction units. Upon reagent solution delivery switch B is closed and the discharge to ground is monitored. Those reaction units that have not receive reagent solution will exhibit a strong and rapid discharge. Those reaction units that have received reagent solution, however, will exhibit a weaker discharge or no observable discharge at all. This is due to the number of charge carriers in the electrode material dissipating throughout the much larger volume of the reagent solution.

In another implementation, the reaction units are charged and left electrically coupled to power source C during reagent solution delivery to the reaction units and subsequently discharged following delivery. Reagent solution that was delivered, however, will have been charged by power source C, and thus these full reaction units will exhibit a strong slow discharge as the charge is dissipated from the reagent solution. In yet another implementation, reaction unit monitoring can be performed following reagent solution delivery. In one example, reaction units can be charged following reagent solution delivery, and upon discharge, the empty units can be readily distinguished from the full units according to the discharge characteristics of the reaction units.

Figure 6A:
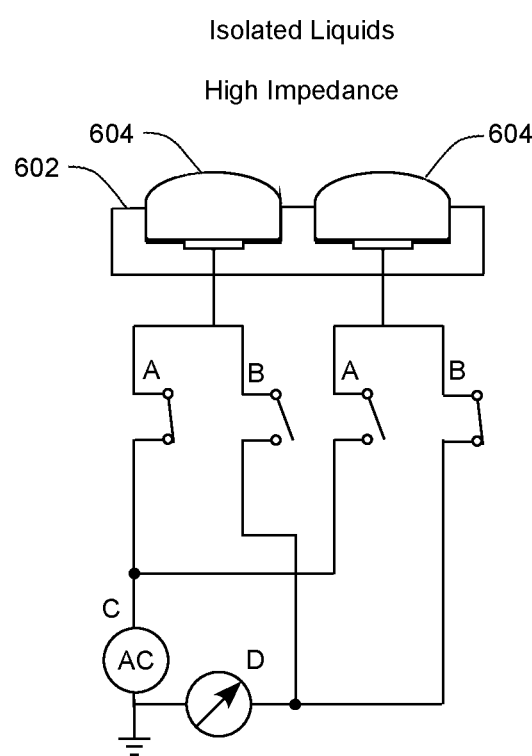
FIG. 6A shows a cross-section view of a pair of reaction units and a spill-over circuit in accordance with an example embodiment.
Figure 6B:
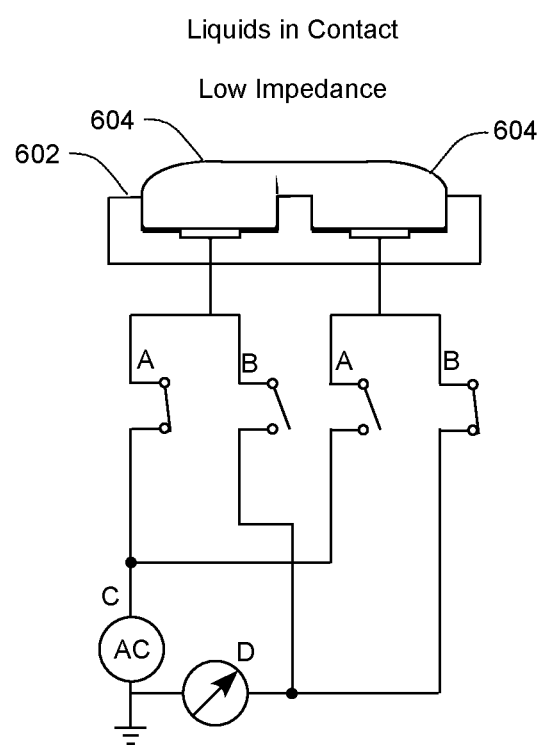
FIG. 6B shows a cross-section view of a pair of reaction units and a spill-over circuit in accordance with an example embodiment.

In another example of a quality control measure, reaction units can be monitored for spill-over between reaction units. Spill-over is a situation where a droplet of reagent solution is in contact with more than one reaction unit, which can result in the synthesis of unintentional DNA sequences that can reduce throughput if not prevented. As is shown in FIG. 6A-B, a spill-over can be detected by measuring the impedance between two adjacent reaction units. Reagent solutions used tend to be polar organic solvents with relatively low impedances compared to air. FIG. 6A shows an adjacent pair of reaction units 602 with a reagent solution droplet 604 in each reaction unit. The pair of reaction units 602 includes a spill-over circuit including a pair of switches A, B for each reaction unit 602 and a common AC power source C and monitor D. When switches A (left) and B (right) are closed and switches B (left) and A (right) are open, current flows to the reaction units 602 and charges the reagent solution droplets 604. The high impedance between the isolated liquids is thus an indication of liquid isolation between the reaction units 602. In the case of FIG. 6B, the contact between the liquids of the reagent solutions 604 between the reaction units 602 is measured as a low impedance by the circuit, thus indicating spill-over has occurred. In such cases, the products from these two reaction units 602 can be recorded as a synthesis error and discarded.

Figure 7:
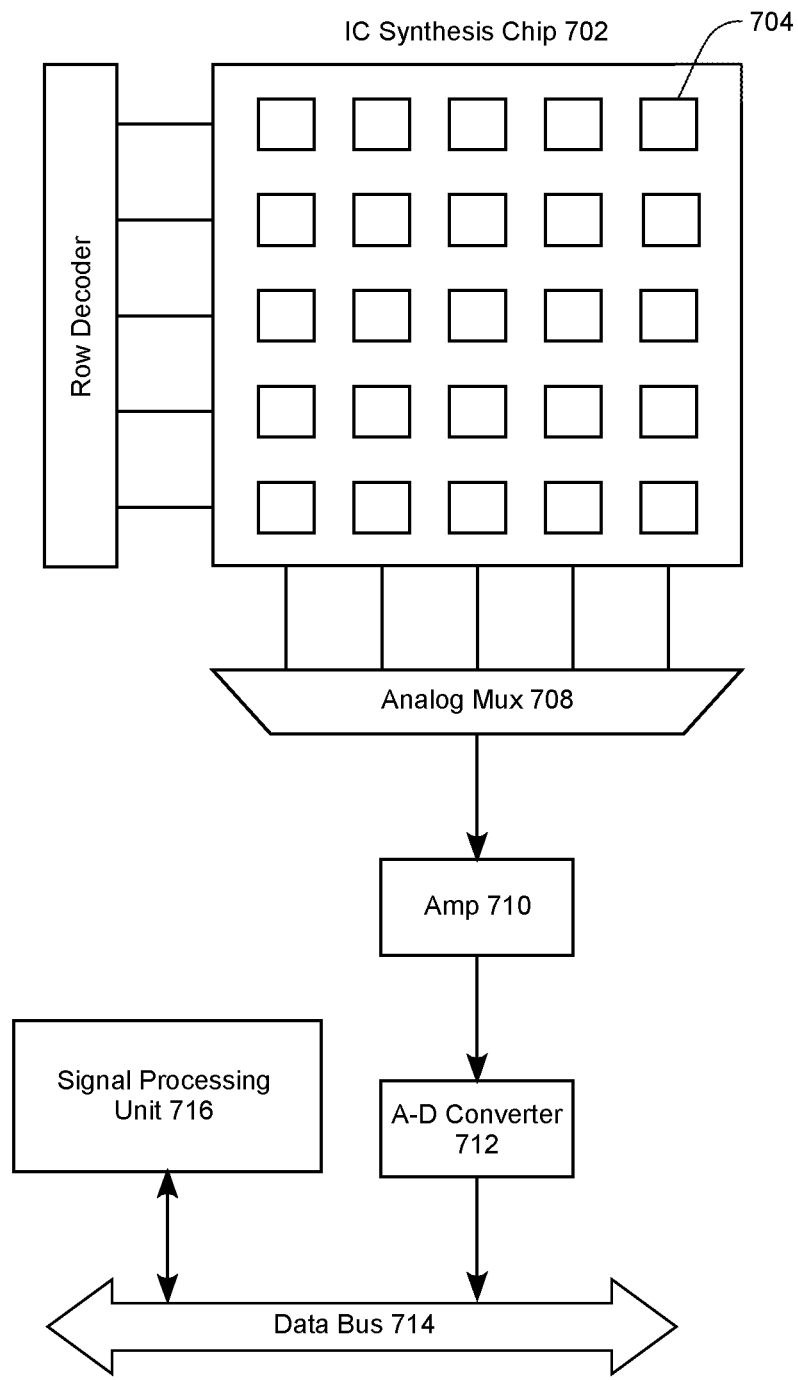
FIG. 7 shows an illustration of an integrated circuit (IC) synthesis chip and quality control circuitry in accordance with an example embodiment.

One example of quality control monitoring across an IC synthesis chip device is shown in FIG. 7. In this example, a synthesis chip 702 is shown having a plurality of reaction units 704 arranged in an array. Each reaction unit 704 includes associated circuitry that enables fill and spill-over monitoring, which are coupled to an analog mux 708. Signals received from the reaction units 704 are thus muxed and then amplified by amplifier 710 and converted to digital signals in an analog-to-digital converter 712. These quality control signals can be sent over a data bus 714 to a signal processing unit 716 that can perform various functions, such as messaging a synthesis control unit to invalidate errored results, feedback for learning to improve pattern recognition of fill errors and spill-over, calibration, noise filtering, and the like. It is noted that, while used in the context of synthesis, a the basic details of the IC synthesis chip are also applicable to the reagent delivery chip.

Figure 8:
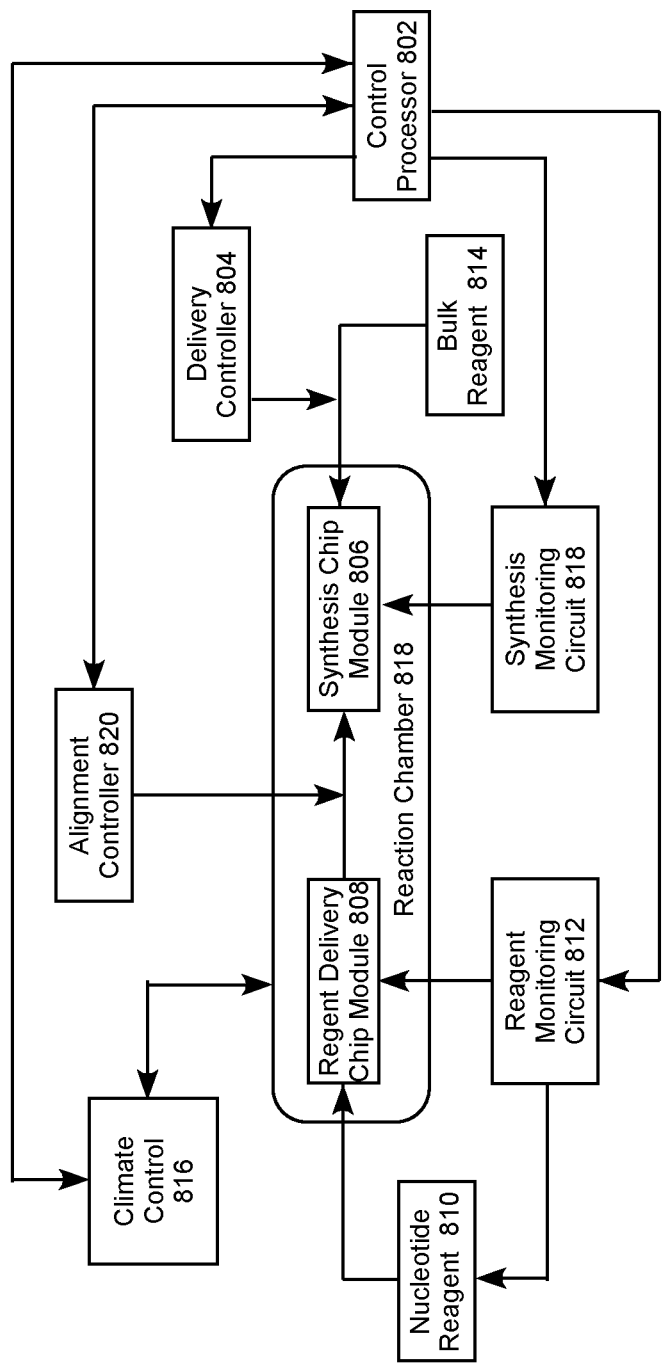
FIG. 8 shows a block diagram of a system for controlling various components of a DNA synthesizing system in accordance with an example embodiment.

FIG. 8 illustrates one example of a control system for implementing DNA synthesis, which can perform all biochemical reactions related to the DNA synthesis automatically. The system can include a control processor 802 for system control, coupled to various system components such as, for example, a delivery controller 904 that can control a synthesis chip module 806 that is in communication with an IC synthesis chip and a reagent delivery chip module 808 in that is in communication with an IC reagent delivery chip. The reagent delivery chip is used to control reagent 810 delivery to the specific reaction units in the DNA synthesis chip, which can occur in multiple cycles for stepwise DNA oligonucleotide synthesis and is monitored by a reagent monitor circuit 812. The reagent monitoring circuit 812 can additionally monitor for fill errors or spill-overs. In addition to electrical detection, the presence of reagents in reaction units can be monitored optically by analyzing fluorescence image patterns.

There are generally two types of reagents to be delivered to the DNA synthesis chip. The first is the group of nucleotide synthesis reagents 810 and the second is referred to as bulk reagents 814, which can be delivered to the DNA synthesis chip either by the electrostatic fluid delivery technique or by direct delivery to the DNA synthesis chip surface through a simple fluidic system. Bulk reagents or solutions can include washing and cleaning solutions, as well as biochemical reagents for oligonucleotide assembly. The biochemical reagents include enzymatic solutions for DNA molecule ligation, extension and detachment. Many biochemical reagents are temperature sensitive and thus should be preserved by refrigeration.

A synthesis monitoring circuit 818 can be included to monitor the synthesis reaction, as well as monitoring for fill errors or spill-overs. In addition to electrical detection, the presence of reagents in reaction units can be monitored optically by analyzing fluorescence image patterns. The system can also include a climate control 816 to control the temperature and humidity of the reaction chamber 818 and provide environmental feedback to the control processor 802. Given the small sizes of the reaction units and the reagent delivery units, it can also be useful to precisely align the two IC chip units to provide accurate fluid delivery. In one example, the system can include an alignment controller and an alignment sensor to control the alignment between the IC chip units. While the specific alignment tolerances will vary from system to system, in one example the alignment accuracy (or misalignment) can be to less than 100 nm in the X-Y direction (horizontal planar alignment) and have a gap between the reaction units and the electrodes of the reagent delivery units of 10 µm or less. Various alignment sensors are contemplated, specific nonlimiting examples of which can include optical sensors, capacitor sensors, or the like.

In one example, a horizontal alignment sensor can be functionally coupled between the synthesis chip and the reagent delivery chip. The horizontal alignment sensor can be used to measure a horizontal planar misalignment between the array of reaction units and the array of reagent delivery units. Additionally, an alignment controller can be functionally coupled to the horizontal alignment sensor, which is configured to receive the horizontal planar misalignment from the horizontal alignment sensor and to compare the horizontal planar misalignment to a misalignment threshold. If the horizontal planar misalignment is greater than the misalignment threshold, the alignment controller is configured to instruct the transport controller to move the transporter in a direction to decrease the horizontal planar misalignment. If the horizontal planar misalignment is less than or equal to the misalignment threshold, the alignment controller is configured to send an alignment acknowledgment to the control processor. A specific misalignment threshold used can vary depending on the design details of a given system or apparatus and is considered to not be limiting. The misalignment threshold, however, should be sufficient to align the reagent delivery chip with the synthesis chip to a degree that allows a successful transfer of fluid droplets from the reagent delivery chip to the synthesis chip. In one specific example, however, the misalignment threshold can be set to 150 nm or less. In another specific example, the misalignment threshold can be set to 100 nm or less.

Turning to DNA synthesis, the presently disclosed technology provides techniques for synthesizing DNA in extremely high amounts through a massively increased parallel synthesis process. In addition to the fluid delivery and DNA synthesis technology described above, techniques for utilizing such technologies to further increase DNA synthesis throughput are provided. Making large DNA molecules, of greater than 100 nt for example, is possible; however, the yield of full-length DNA decreases as the length of the DNA molecule being synthesized increases. For a 200 nt sequence, for example, the full-length yield will drop to 13% at 99% stepwise efficiency. For the same reaction efficiency, however, the full-length yield of 50 nt DNA molecule can be about 60% at 99% stepwise efficiency. Generation of larger DNA sequences, however, can be accomplished by synthesizing multiple shorter oligonucleotide segments of the sequence at much higher yields, which are then coupled together to form the larger DNA molecule. This synthesis technique can be performed on an IC chip as described above for massively parallel DNA throughput.

Using the properties of exonuclease resistance and selective cleavage, several DNA oligomers can be assembled specifically and sequentially to form a longer DNA molecule. In general, a repeating process can be performed for each DNA oligomer, which can include DNA annealing: hybridizing a DNA segment to a desired target DNA segment through 3' complementary regions;

Extension: extending the 3' end that is complementary to the target DNA segment to form double-stranded DNA.

Cleavage: selectively cleaving the double-stranded DNA at a specific site using a double-stranded-specific enzyme.

FIGS. 9A-H illustrate one example of DNA synthesis on the surface of an IC chip synthesizer. For this example, five reaction sites numbered 0-4 are used (see FIG. 9A). It is noted that the number of reaction sites, as well as their illustrated arrangement, is merely exemplary, and various numbers and arrangements of reaction sites are contemplated. A DNA oligonucleotide segment (DNA segment) is synthesized in a stepwise manner from each of the reaction sites, as is shown in FIG. 9B, and each DNA segment is numbered according to the reaction site from which it was synthesized. While only one DNA segment is shown being synthesized from each reaction site, this is to avoid obscuring the details shown in the figure. In practice, many of the same DNA segments are synthesized in each reaction site. The DNA segments are portions of a larger DNA sequence being synthesized, and thus must be coupled together in a specific order to generate the proper DNA sequence. Furthermore, each DNA segment can be of any length capable of synthesis, with the understanding that the longer a DNA segment the lower the yield.

Solid-phase DNA synthesis can be accomplished by a variety of techniques, which are not limiting. In one example, a phosphoramidite chemistry technique can be utilized that includes a four-step DNA oligonucleotide (DNA sequence) synthesis process. Initially, a dimethoxytrityl (DMT)-protected nucleoside phosphoramidite attached to a support surface is deprotected using an acid. Next, the unprotected 5' OH site is subject to base coupling with a DMT-protected phosphoramidite using tetrazole activator to form a phosphite triester. As a next step, any remaining unreacted 5' sites are acetylated (i.e., capped) to prevent further chain extension. Subsequently, the phosphite triester is oxidized to phosphate using aqueous iodine to produce a cyanoethyl-protected phosphate backbone in preparation for the next round of extension of the DNA sequence. The DNA sequence is deprotected, and the process is repeated. When the synthesis is complete, the DNA sequence is cleaved from the support surface and deprotected. Alternately, DNA molecules can be synthesized from the 5' (attached to the solid support) to the 3' direction.

The larger DNA sequence being synthesized is made up of the DNA segments arranged in a specific order, and thus the DNA segments must be coupled together in this specific order to generate the correct DNA sequence. This can be achieved through complementary strand hybridization at corresponding 3' ends of adjacent DNA segments in the sequence. After chemical synthesis of the DNA segments, a DNA "bridge" segment is introduced to associate the initial two DNA segments together in their proper sequence, in this case DNA segments 0 and 1. The bridge DNA is utilized to bridge the distance between reaction site 0 and reaction site 1. To ensure the proper order of DNA segments 0 and 1, the bridge DNA includes free ss terminal ends that specifically hybridize with the ends of these two DNA segments. FIG. 9C shows the bridge DNA (Br) segment hybridized to the ends of DNA segments 0 and 1. Free ss terminal end or free terminal end is a single-stranded region with >1 nt protruding from the 3' end of a dsDNA sequence or molecule. In one example, the protruding end is in the range of 5 to 50 nt long, while in another example the protruding end is in the range of 10 to 30 nt long.

A bridge DNA segment is a double-stranded (ds) DNA molecule that can have a length that varies depending on various characteristics of the reaction site array, such as for example, the length of the synthesized DNA segments, the distance between sites containing synthesized DNA segments that the bridge DNA segment is intended to probe, and the like. In some examples, however, the bridge DNA segment can be sufficiently long to successfully hybridize with the two DNA segments that it is intended to bridge. In one specific example, the bridge DNA segment can have a physical length from about 1 to about 2 µm. For example, a 5K nt long DNA segment is about 1.7 µm. In one example, a bridge DNA segment can associate 2 DNA segments synthesized in 2 different locations separated by less than 1.5 µm. Additionally, the bridge DNA segment can have sequence information for identification (ID) or indexing purpose for a set of related DNA segments to be assembled. In some examples, the ends (typically 3' protruding ends) of a bridge DNA segment and the synthesized DNA segments are so designed that the same or different bridge DNA segments can be used for the entire array of synthesized DNA segments. Additionally, the bridge DNA can be chemically synthesized DNA, derived from natural DNA, modified from natural DNA, or the like. For example, the bridge DNA can be a segment of a genomic DNA of a bacterium, a virus, a plant or an animal.

Figure 10:
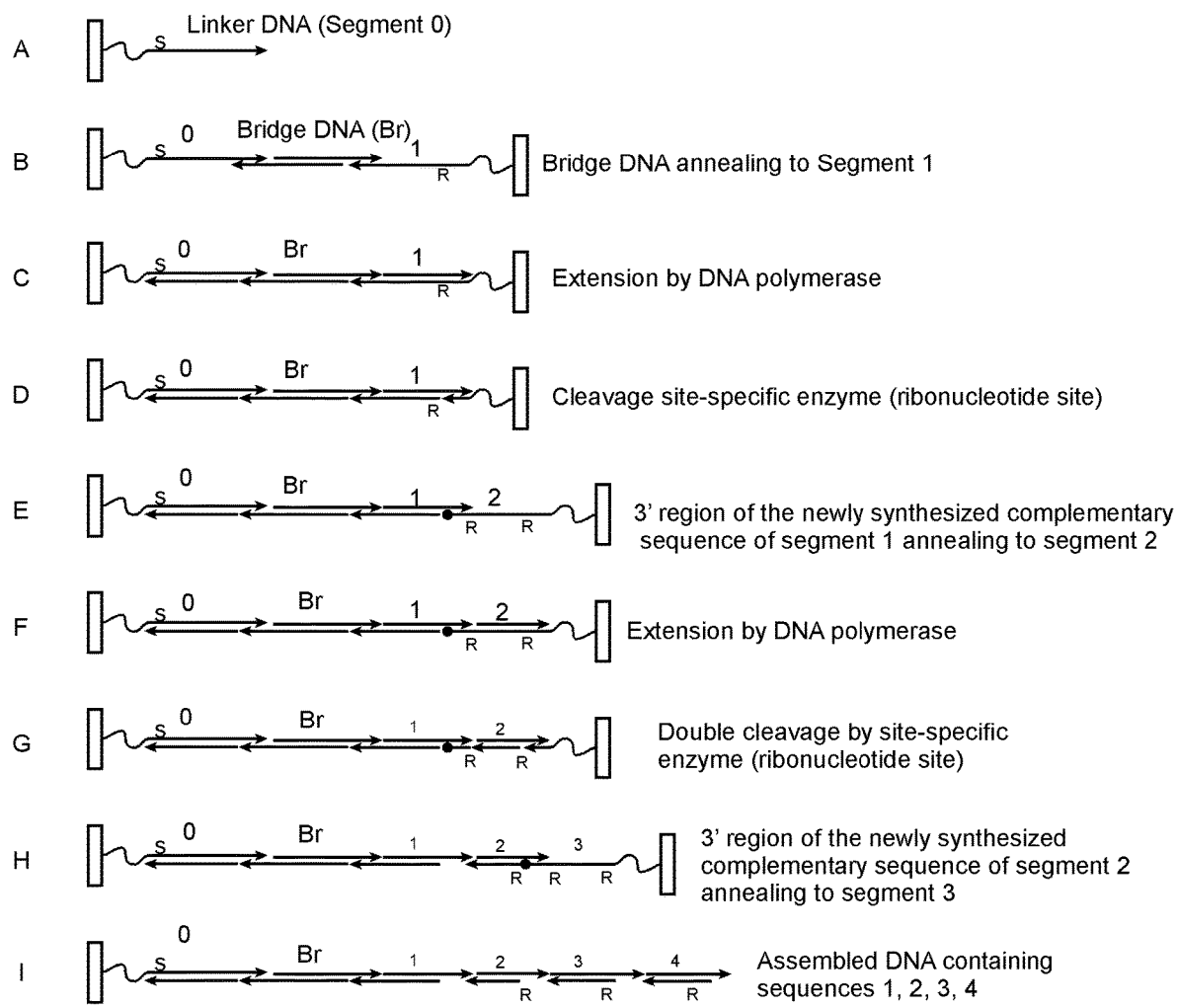
FIG. 10 shows an illustration of a reactions to generate an assembled DNA oligonucleotide from a plurality of DNA segments in accordance with an example embodiment.

FIG. 10 illustrates an example of the assembly of a DNA sequence from multiple DNA segments and will be used in conjunction with FIGS. 9A-H in describing examples of such assembly. Line A of FIG. 10 shows a rotated view of a reaction site surface with a linker DNA segment (corresponding to sequence 0 of FIG. 9) synthesized therefrom. The location marked "S" represents a cleavage site such as, for example, and endonuclease IV cleavage site. Following hybridization of the bridge DNA segment with the ends of DNA segments 0 and 1, a DNA polymerase is used to create dsDNA molecules from segments 0 and 1. Nonlimiting examples of DNA polymerases can include T4 DNA polymerase, Bst1 DNA polymerase, Pfu DNA polymerase, and the like. Line B of FIG. 10 shows the bridge DNA hybridized with the ends of segments 0 and 1, and line C shows dsDNA is created from the bridge DNA along each of the single-stranded segments.

It is noted that, in this example, segment 0 is used as a linker DNA to provide an attachment to the solid surface during DNA sequence assembly. In some examples, the function of segment 0 can be limited to its role in supporting the DNA assembly, while in other examples segment 0 can have a sequence that is a portion of the DNA sequence to be assembled, and thus be ultimately incorporated into the fully assembled DNA. In other examples, segment 0 can include sequence(s) used in further processing, such as primer sites, plasmid incorporation sites, barcoding for tracking, and the like.

As shown in line D of FIG. 10, the dsDNA segment 1 is selectively cleaved from reaction site 1, leaving the ds linker DNA segment attached to reaction site 0. Ligation can be performed before or after the polymerase reaction to stabilize the DNA molecule between the bridge DNA segment and linker DNA segment. Further DNA sequence assembly is performed through a sequential "bridge-DNA-walking" technique. The cleaved end of dsDNA segment 1 has a single-stranded 3' protruding region that hybridizes to the 3' end of the single-stranded DNA segment at reaction site 2. FIG. 9D shows DNA segment 0 coupled to reaction site 0, the bridge DNA coupled between DNA segment 0 and DNA segment 1, and DNA segment 2 coupled to DNA segment 1 and to reaction site 2. Line E of FIG. 10 shows DNA segment 1 annealing to DNA segment 2. DNA polymerase is used to create a dsDNA molecule from the single-stranded DNA segment 2 (line F), followed by selective cleavage from reaction site 2, again leaving the ds linker DNA (segment 0) attached to reaction site 0. This process continues for DNA segments 3 and 4, as is shown in FIGS. 9F-G and lines H and I of FIG. 10, resulting in a dsDNA molecule coupled to reaction site 1 and having the sequence of DNA segment 0, bridge DNA, DNA segment 1, DNA segment 2, DNA segment 3, and DNA segment 4. The order of the DNA assembly is determined by the complementarity end regions that are pre-determined or designed before DNA oligonucleotide synthesis. The assembled product is a dsDNA or a partially dsDNA molecule with one strand having a continuous sequence. The DNA assembly can be halted at any step, depending on the final product design. When PCR primer sites are introduced into the DNA sequences, assembled DNA molecules can be enriched by PCR reactions. Additionally, the DNA product can be PCR-purified from truncated sequences.

Figure 11:
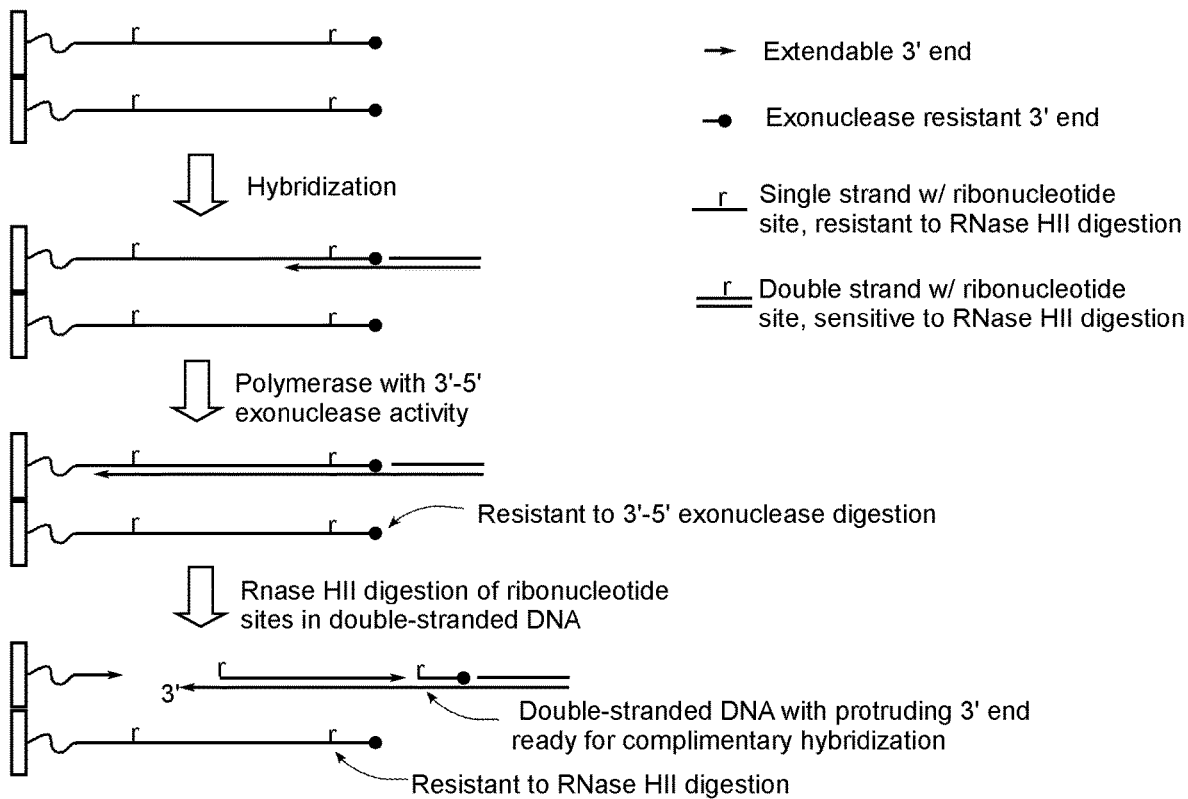
FIG. 11 shows an illustration of various features of DNA synthesis that allow selective cleavage at various points in the technique in accordance with an example embodiment.

FIG. 11 shows some of the features of DNA synthesis that allow selective cleavage at various points in the technique. Following hybridization, DNA polymerase extension is used to create a dsDNA molecule. The synthesized DNA molecules should be resistant to 3'-5' exonuclease in order to not be degraded during DNA polymerization with a proofreading DNA polymerase on other molecules. There are many different methods that can be used to render the 3' end nuclease resistant (IDT-DNA, Integrated DNA Technologies). For example, nuclease-resistance can be accomplished by modifications in bases, in the ribose, or in the phosphodiester bond of the molecule. DNA has one or two 3'-terminal phosphorothioate (PTO) modifications that are resistant to the 3'→5' exonuclease activity of proofreading DNA polymerases, such as Klenow Fragment and phi29 DNA polymerase, for example. In the polymerase reaction, ribonucleotide-containing DNA templates can be copied by DNA polymerases.

Following synthesis, the DNA molecules can be selectively cleaved at specific sites using site-specific enzymes. Nonlimiting examples of such sites can include ribonucleotide sites, methylated sites, special restriction enzyme sites, abasic sites, apurinic/apyrimidinic (AP), and the like. For example, endonuclease IV can act on a variety of oxidative damage sites in DNA. The enzyme is apurinic/apyrimidinic (AP) endonuclease, which will hydrolyze intact AP sites in DNA. AP sites are then cleaved at the first phosphodiester bond that is 5' to the lesion leaving a hydroxyl group at the 3' terminus and a deoxyribose 5'-phosphate at the 5' terminus. An abasic site can be created at the deoxyribosyl uridine site after digestion by Uracil-DNA-glycosylase.

Selective cleavage can also be performed with Ribonuclease HII (RNase HII), which is an endoribonuclease that preferentially nicks 5' to a ribonucleotide within the context of a DNA duplex. The enzyme leaves 5' phosphate and 3' hydroxyl ends. UV sensitive sites containing a modified base that can be cleaved by UV exposure can additionally be used. Other modified or non-natural DNA nucleotides can also be cleaved chemically (pH, salts, etc.), biochemically (enzymes), or physically (heat, etc.).

Figure 12:
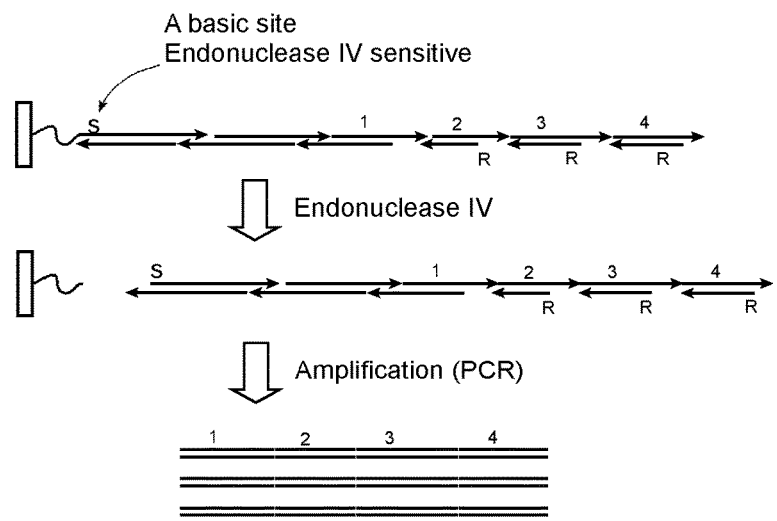
FIG. 12 shows an illustration of post assembly processing of a DNA oligonucleotide following assembly in accordance with an example embodiment.

FIG. 12 shows an example of post assembly processing of the product described in FIG. 10. The assembled DNA coupled to reaction site 0 can be selectively cleaved from the surface using any known technique, provided the cleavage is specific. FIG. 12 shows an example of an abasic site (AP site) present in the DNA molecules of near reaction site 0, which can be cleaved using endonuclease IV. In some examples the bridge DNA can be selectively cleaved from the other DNA sequence. Such cleavage can be performed using selective restriction enzyme digestions or any other known cleavage technique, provided that the digestion site is unique to the bridge DNA. Since all DNA sequences are known before synthesis and assembly, such unique site(s) can be determined with computer modeling. FIG. 9H shows the assembled DNA molecule having been cleaved from reaction site 0 and having the bridge DNA excised. The assembled DNA molecule can be cyclized as shown or left in a linear state, either with or without DNA segment 0. Additionally, the cleaved DNA can be cyclized before or after the removal of the bridge DNA or any portion of the bridge DNA. Cyclized DNA can be used for rolling circle amplification to generate single-stranded concatemers (a long continuous DNA molecule that contains multiple copies of the same DNA sequence linked in series), which can be used, for example, in DNA sequencing reactions. The assembled DNA can also be detached and amplified by PCR reaction, which also has many uses including DNA sequencing reactions.

EXAMPLES

The following examples pertain to specific embodiments and point out specific features, elements, or steps that can be used or otherwise combined in achieving such embodiments.

In one example, there is provided a deoxyribonucleic acid (DNA) synthesis apparatus, comprising a synthesizer chip including an array of reaction units arranged in a predetermined pattern, each reaction unit including a reaction surface, an integrated circuit (IC) array of reaction electrodes arranged in the predetermined pattern such that each reaction unit includes a reaction electrode, and a synthesizer chip controller coupled to the IC array of reaction electrodes and configured to address and control each of the reaction electrodes individually. The apparatus also includes a reagent delivery chip positionable above the synthesizer chip, including an array of reagent delivery units arranged in the predetermined pattern, each reagent delivery unit configured to receive and deliver a droplet of reagent fluid having a volume of 1 picoliter (pL) or less, an IC array of reagent electrodes arranged in the predetermined pattern such that each reagent delivery unit includes a reagent electrode, and a reagent delivery chip controller communicatively coupled to the IC array of reagent electrodes and configured to address and control each of the reagent electrodes individually.

In one example, the apparatus further comprises a control processor communicatively coupled to the synthesis delivery chip controller and the reagent delivery chip controller and configured to control operation of the synthesizer chip and the reagent delivery chip.

In one example, the apparatus further comprises a transporter coupled to the reagent delivery chip and configured to transport the reagent delivery chip back and forth from a position above the synthesizer chip to a position above a reagent solution tray and a transport controller communicatively coupled to the transporter and configured to instruct the transporter to move the reagent delivery chip back and forth from the position above the synthesizer chip to the position above the reagent solution tray.

In one example apparatus, when the reagent delivery chip is at the position over the reagent solution tray, the reagent delivery controller is further configured to electrically charge a reagent solution in the reagent tray with a first charge, electrically charge the reagent electrodes in at least a portion of the array of reagent delivery units with a second charge having a charge polarity opposite the first charge, where the second charge is sufficient to transport portions of the charged reagent solution to each oppositely charged reagent electrode as reagent solution droplets, where each reagent solution droplet has a volume of 1 pL or less and discharge the reagent electrodes and the reagent solution droplets. When the reagent delivery chip is at the position over the synthesizer chip, the reagent delivery controller is further configured to electrically charge each reagent solution droplet in the at least a portion of the array of reagent delivery units with a third charge, electrically charge each reaction electrodes corresponding to a reagent delivery unit having a reagent solution droplet with a fourth charge having a charge polarity opposite to the third charge, where the fourth charge is sufficient to transport each charged reagent solution droplet to the corresponding oppositely charged reaction electrode, and discharge the charged reagent solution droplets.

In one example apparatus, the reagent delivery controller is further configured to receive a reagent request for delivery to a portion of the array of reaction units, instruct the transport controller to move the transporter with the reagent delivery chip to the position above the reagent solution tray, fill a portion of the array of reagent delivery units corresponding to the portion of the array of reaction units with reagent solution droplets, instruct the transport controller to move the transporter to the position over the synthesis chip, and deliver the reagent solution droplets from the portion of the array of reagent delivery units to the corresponding portion of the array of reaction units.

In one example, the apparatus further comprises a horizontal alignment sensor functionally coupled between the synthesis chip and the reagent delivery chip configured to measure a horizontal planar misalignment between the array of reaction units and the array of reagent delivery units and an alignment controller functionally coupled to the horizontal alignment sensor configured to receive the horizontal planar misalignment from the horizontal alignment sensor and compare the horizontal planar misalignment to a misalignment threshold. If the horizontal planar misalignment is greater than the misalignment threshold, the alignment controller is configured to instruct the transport controller to move the transporter in a direction to decrease the horizontal planar misalignment. If the horizontal planar misalignment is less than or equal to the misalignment threshold, the alignment controller is configured to send an alignment acknowledgment to the control processor.

In one example apparatus, the misalignment threshold is set at 150 nm or less.

In one example apparatus, the misalignment threshold is set at 100 nm or less.

In one example apparatus, the reagent request is for a different reagent, and the reagent delivery controller is further configured to instruct the transport controller to move the transporter with the reagent delivery chip to a different position above a different reagent solution tray, fill a portion of the array of reagent delivery units corresponding to the portion of the array of reaction units with different reagent solution droplets, instruct the transport controller to move the transporter to the position over the synthesis chip, and deliver the different reagent solution droplets from the portion of the array of reagent delivery units to the corresponding portion of the array of reaction units.

In one example apparatus, each reaction surface of the array of reaction units is positioned at a bottom of a reaction well in each reaction unit.

In one example apparatus, each reaction well has a diameter of less than 35 μm.

In one example apparatus, each reaction well has a diameter of from 0.1 μm to 12 μm.

In one example apparatus, each reaction well has a diameter of from 0.1 μm to 10 μm.

In one example apparatus, each reaction well has a diameter of from 0.1 μm to 5 μm.

In one example apparatus, each reaction well has a diameter of from 0.1 μm to 1 μm.

In one example apparatus, the IC array of reagent electrodes is a complimentary metal-oxide-semiconductor (CMOS) array of reagent electrodes and the IC array of reaction electrodes is a CMOS array of reaction electrodes.

In one example, the apparatus further comprises a fill detection circuit functionally coupled to each reaction electrode in the IC array of reaction electrodes, the fill detection circuit being configured to detect a presence or an absence of a droplet of reagent solution at the associated reaction electrode.

In one example, the apparatus further comprises a spill-over detection circuit functionally coupled between each adjacent pair of reaction electrodes in the IC array of reaction electrodes, the spill-over detection circuit being configured to detect a liquid contact between adjacent pairs of reaction electrodes.

In one example, there is provided a deoxyribonucleic acid (DNA) synthesis system, comprising a DNA synthesis apparatus, comprising a synthesizer chip including an array of reaction units arranged in a predetermined pattern, each reaction unit including a reaction surface, an integrated circuit (IC) array of reaction electrodes arranged in the predetermined pattern such that each reaction unit includes a reaction electrode, and a synthesizer chip controller coupled to the IC array of reaction electrodes and configured to address and control each of the reaction electrodes individually. The apparatus also includes a reagent delivery chip positionable above the synthesizer chip, including an array of reagent delivery units arranged in the predetermined pattern, each reagent delivery unit configured to receive and deliver a droplet of reagent fluid having a volume of 1 picoliter (pL) or less, an IC array of reagent electrodes arranged in the predetermined pattern such that each reagent delivery unit includes a reagent electrode, and a reagent delivery chip controller communicatively coupled to the IC array of reagent electrodes and configured to address and control each of the reagent electrodes individually. The DNA synthesis system further includes a control processor configured to control operation of the synthesizer chip and the reagent delivery chip, a transporter coupled to the reagent delivery chip and configured to transport the reagent delivery chip back and forth from a position above the synthesizer chip to a position above a reagent solution tray, and a transport controller communicatively coupled to the transporter and configured to instruct the transporter to move the reagent delivery chip back and forth from the position above the synthesizer chip to the position above the reagent solution tray. The system can also include a fill detection circuit functionally coupled to each reaction electrode in the IC array of reaction electrodes, the fill detection circuit being configured to detect a presence or an absence of a droplet of reagent solution at the associated reaction electrode and a spill-over detection circuit functionally coupled between each adjacent pair of reaction electrodes in the IC array of reaction electrodes, the spill-over detection circuit being configured to detect a liquid contact between adjacent pairs of reaction electrodes.

In one example system, when the reagent delivery chip is at the position over the reagent solution tray, the reagent delivery controller is further configured to electrically charge a reagent solution in the reagent tray with a first charge, electrically charge the reagent electrodes in at least a portion of the array of reagent delivery units with a second charge having a charge polarity opposite the first charge, where the second charge is sufficient to transport portions of the charged reagent solution to each oppositely charged reagent electrode as reagent solution droplets, where each reagent solution droplet has a volume of 1 pL or less and discharge the reagent electrodes and the reagent solution droplets. When the reagent delivery chip is at the position over the synthesizer chip, the reagent delivery controller is further configured to electrically charge each reagent solution droplet in the at least a portion of the array of reagent delivery units with a third charge, electrically charge each reaction electrodes corresponding to a reagent delivery unit having a reagent solution droplet with a fourth charge having a charge polarity opposite to the third charge, where the fourth charge is sufficient to transport each charged reagent solution droplet to the corresponding oppositely charged reaction electrode, and discharge the charged reagent solution droplets.

In one example system, the reagent delivery controller is further configured to receive a reagent request for delivery to a portion of the array of reaction units, instruct the transport controller to move the transporter with the reagent delivery chip to the position above the reagent solution tray, fill a portion of the array of reagent delivery units corresponding to the portion of the array of reaction units with reagent solution droplets, instruct the transport controller to move the transporter to the position over the synthesis chip, and deliver the reagent solution droplets from the portion of the array of reagent delivery units to the corresponding portion of the array of reaction units.

In one example, the system further comprises a horizontal alignment sensor functionally coupled between the synthesis chip and the reagent delivery chip configured to measure a horizontal planar misalignment between the array of reaction units and the array of reagent delivery units and an alignment controller functionally coupled to the horizontal alignment sensor configured to receive the horizontal planar misalignment from the horizontal alignment sensor and compare the horizontal planar misalignment to a misalignment threshold. If the horizontal planar misalignment is greater than the misalignment threshold, the alignment controller is configured to instruct the transport controller to move the transporter in a direction to decrease the horizontal planar misalignment. If the horizontal planar misalignment is less than or equal to the misalignment threshold, the alignment controller is configured to send an alignment acknowledgment to the control processor.

In one example system, the misalignment threshold is set at 150 nm or less.

In one example system, the misalignment threshold is set at 100 nm or less.

In one example system, the reagent request is for a different reagent, and the reagent delivery controller is further configured to instruct the transport controller to move the transporter with the reagent delivery chip to a different position above a different reagent solution tray, fill a portion of the array of reagent delivery units corresponding to the portion of the array of reaction units with different reagent solution droplets, instruct the transport controller to move the transporter to the position over the synthesis chip, and deliver the different reagent solution droplets from the portion of the array of reagent delivery units to the corresponding portion of the array of reaction units.

In one example system, each reaction surface of the array of reaction units is positioned at a bottom of a reaction well in each reaction unit.

In one example system, each reaction well has a diameter of less than 35 µm.

In one example system, each reaction well has a diameter of from 0.1 µm to 12 µm.

In one example system, each reaction well has a diameter of from 0.1 µm to 10 µm.

In one example system, each reaction well has a diameter of from 0.1 µm to 5 µm.

In one example system, each reaction well has a diameter of from 0.1 µm to 1 µm.

In one example system, the IC array of reagent electrodes is a complimentary metal-oxide-semiconductor (CMOS) array of reagent electrodes and the IC array of reaction electrodes is a CMOS array of reaction electrodes.

In one example, the system further comprises a fill detection circuit functionally coupled to each reaction electrode in the IC array of reaction electrodes, the fill detection circuit being configured to detect a presence or an absence of a droplet of reagent solution at the associated reaction electrode.

In one example, the system further comprises a spill-over detection circuit functionally coupled between each adjacent pair of reaction electrodes in the IC array of reaction electrodes, the spill-over detection circuit being configured to detect a liquid contact between adjacent pairs of reaction electrodes.

In one example, there is provided a method of synthesizing a deoxyribonucleic acid (DNA) oligonucleotide, comprising electronically dividing a DNA oligonucleotide sequence into a plurality of segments having an order corresponding to the DNA oligonucleotide sequence, and each of the plurality of segments having a hybridization sequence at each end such that annealing is specific according to the segment order, synthesizing simultaneously each segment as a DNA segment along with a linker DNA, each physically anchored in fluidic isolation, from different reaction surfaces of a plurality of spatially aggregated reaction surfaces, and fluidically coupling the spatially aggregated reaction surfaces in a fluid environment. The method further includes introducing a double-stranded (ds) bridge DNA into the fluid environment, the ds bridge DNA having exposed single-stranded (ss) terminal ends to specifically anneal between the linker DNA and a first DNA segment of the segment order, generating a ds first DNA segment from the first DNA segment, cleaving the ds first DNA segment from the associated reaction surface to generate a first oligonucleotide sequence extending from the reaction surface and including the linker DNA anchored to the reaction surface, the ds bridge DNA, and the ds first DNA segment having a free terminal end.

In one example, the method further comprises annealing the free terminal end of the ds first DNA segment to a free terminal end of a subsequent DNA segment at corresponding hybridization sequences according to the segment order, the subsequent DNA segment physically anchored to the reaction surface, generating a ds subsequent DNA segment from the subsequent DNA segment, and cleaving the ds subsequent DNA segment from the associated reaction surface to generate a subsequent oligonucleotide sequence extending from the reaction surface and including the linker DNA anchored to the reaction surface, the ds bridge DNA, the ds first DNA segment, and the ds subsequent DNA segment having a free terminal end.

In one example, the method further comprises repeating the annealing, the generating, and the cleaving for each remaining next subsequent DNA segment according to the segment order to generate a bulk oligonucleotide sequence extending from the reaction surface and including the linker DNA anchored to the reaction surface, the ds bridge DNA, the ds first DNA segment, the ds subsequent DNA segment, and all remaining ds next subsequent DNA segments according to the segment order.

In one example, the method further comprises cleaving the bulk oligonucleotide sequence from the associated reaction surface.

In one example, the method further comprises cyclizing the bulk oligonucleotide sequence and cleaving at least a portion of the ds bridge DNA from the cyclized bulk oligonucleotide sequence.

In one example method, each DNA segment is less than or equal to 100 nucleotides in length.

In one example, wherein in generating the ds first DNA segment from the first DNA segment, the method further comprises extending the ss terminal end of the ds bridge DNA hybridized to the first DNA segment along the first DNA segment length using a DNA polymerase.

In one example, the method further comprises extending the ss terminal end of the ds bridge DNA hybridized to the linker DNA along the linker DNA length using a DNA polymerase.

In one example, wherein in cleaving the ds first DNA segment from the associated reaction surface, the method further comprises cleaving the ds first DNA segment at a ds restriction site near the reaction surface with an enzyme specific for the ds restriction site.

In one example, wherein to cleave the bulk oligonucleotide sequence from the associated reaction surface the method further comprises cleaving the ds linker DNA at a ds restriction site near the reaction surface with an enzyme specific for the ds restriction site.

What is claimed is:

1. A deoxyribonucleic acid (DNA) synthesis apparatus, comprising:
   a synthesizer chip, further comprising:
      an array of reaction units arranged in a predetermined pattern, each reaction unit including a reaction surface;
      an integrated circuit (IC) array of reaction electrodes arranged in the predetermined pattern such that each reaction unit includes a reaction electrode; and
      a synthesizer chip controller coupled to the IC array of reaction electrodes and configured to address and control each of the reaction electrodes individually; and
   a reagent delivery chip positionable above the synthesizer chip, comprising:
      an array of reagent delivery units arranged in the predetermined pattern, each reagent delivery unit configured to receive and deliver a droplet of reagent fluid having a volume of 1 picoliter (pL) or less;
      an IC array of reagent electrodes arranged in the predetermined pattern such that each reagent delivery unit includes a reagent electrode; and
      a reagent delivery chip controller communicatively coupled to the IC array of reagent electrodes and configured to address and control each of the reagent electrodes individually.

2. The apparatus of claim 1, further comprising a control processor communicatively coupled to the synthesizer chip and the reagent delivery chip and configured to control operation of the synthesizer chip and the reagent delivery chip.

3. The apparatus of claim 1, further comprising:
   a transporter coupled to the reagent delivery chip and configured to transport the reagent delivery chip back and forth from a position above the synthesizer chip to a position above a reagent solution tray; and
   a transport controller communicatively coupled to the transporter and configured to instruct the transporter to move the reagent delivery chip back and forth from the position above the synthesizer chip to the position above the reagent solution tray.

4. The apparatus of claim 3, wherein:
   when the reagent delivery chip is at the position over the reagent solution tray, the reagent delivery chip is further configured to:
      electrically charge a reagent solution in the reagent tray with a first charge;
      electrically charge the reagent electrodes in at least a portion of the array of reagent delivery units with a second charge having a charge polarity opposite the first charge, where the second charge is sufficient to transport portions of the charged reagent solution to each oppositely charged reagent electrode as reagent solution droplets, where each reagent solution droplet has a volume of 1 pL or less; and
      discharge the reagent electrodes and the reagent solution droplets; and
   when the reagent delivery chip is at the position over the synthesizer chip, the reagent delivery chip is further configured to:

electrically charge each reagent solution droplet in the at least a portion of the array of reagent delivery units with a third charge;
electrically charge each reaction electrode corresponding to a reagent delivery unit having a reagent solution droplet with a fourth charge having a charge polarity opposite to the third charge, where the fourth charge is sufficient to transport each charged reagent solution droplet to the corresponding oppositely charged reaction electrode; and
discharge the charged reagent solution droplets.

5. The apparatus of claim 4, wherein the reagent delivery chip is further configured to:
receive a reagent request for delivery to a portion of the array of reaction units;
instruct the transport controller to move the transporter with the reagent delivery chip to the position above the reagent solution tray;
fill a portion of the array of reagent delivery units corresponding to the portion of the array of reaction units with reagent solution droplets;
instruct the transport controller to move the transporter to the position over the synthesizer chip; and
deliver the reagent solution droplets from the portion of the array of reagent delivery units to the corresponding portion of the array of reaction units.

6. The apparatus of claim 5, further comprising:
a horizontal alignment sensor functionally coupled between the synthesizer chip and the reagent delivery chip configured to measure a horizontal planar misalignment between the array of reaction units and the array of reagent delivery units; and
an alignment controller functionally coupled to the horizontal alignment sensor configured to:
receive the horizontal planar misalignment from the horizontal alignment sensor; and
compare the horizontal planar misalignment to a misalignment threshold;
if the horizontal planar misalignment is greater than the misalignment threshold, the alignment controller is configured to instruct the transport controller to move the transporter in a direction to decrease the horizontal planar misalignment; and
if the horizontal planar misalignment is less than or equal to the misalignment threshold, the alignment controller is configured to send an alignment acknowledgment to the reagent delivery chip.

7. The apparatus of claim 6, wherein the misalignment threshold is set at 100 nm or less.

8. The apparatus of claim 5, wherein the reagent request is for a different reagent, and the reagent delivery chip is further configured to:
instruct the transport controller to move the transporter with the reagent delivery chip to a different position above a different reagent solution tray;
fill a portion of the array of reagent delivery units corresponding to the portion of the array of reaction units with different reagent solution droplets;
instruct the transport controller to move the transporter to the position over the synthesizer chip; and
deliver the different reagent solution droplets from the portion of the array of reagent delivery units to the corresponding portion of the array of reaction units.

9. The apparatus of claim 1, where each reaction surface of the array of reaction units is positioned at a bottom of a reaction well in each reaction unit.

10. The apparatus of claim 9, wherein each reaction well has a diameter of less than 35 μm.

11. The apparatus of claim 1, wherein the IC array of reagent electrodes is a complimentary metal-oxide-semiconductor (CMOS) array of reagent electrodes and the IC array of reaction electrodes is a CMOS array of reaction electrodes.

12. The apparatus of claim 1, further comprising:
a fill detection circuit functionally coupled to each reaction electrode in the IC array of reaction electrodes, the fill detection circuit being configured to detect a presence or an absence of a droplet of reagent solution at the associated reaction electrode; and
a spill-over detection circuit functionally coupled between each adjacent pair of reaction electrodes in the IC array of reaction electrodes, the spill-over detection circuit being configured to detect a liquid contact between adjacent pairs of reaction electrodes.

13. A deoxyribonucleic acid (DNA) synthesis system, comprising:
the DNA synthesis apparatus of claim 1;
a control processor configured to control operation of the synthesizer chip and the reagent delivery chip;
a transporter coupled to the reagent delivery chip and configured to transport the reagent delivery chip back and forth from a position above the synthesizer chip to a position above a reagent solution tray;
a transport controller communicatively coupled to the transporter and configured to instruct the transporter to move the reagent delivery chip back and forth from the position above the synthesizer chip to the position above the reagent solution tray;
a fill detection circuit functionally coupled to each reaction electrode in the IC array of reaction electrodes, the fill detection circuit being configured to detect a presence or an absence of a droplet of reagent solution at the associated reaction electrode; and
a spill-over detection circuit functionally coupled between each adjacent pair of reaction electrodes in the IC array of reaction electrodes, the spill-over detection circuit being configured to detect a liquid contact between adjacent pairs of reaction electrodes.

14. The system of claim 13, wherein:
when the reagent delivery chip is at the position over the reagent solution tray, the reagent delivery chip is further configured to:
electrically charge a reagent solution in the reagent solution tray with a first charge;
electrically charge the reagent electrodes in at least a portion of the array of reagent delivery units with a second charge having a charge polarity opposite the first charge, where the second charge is sufficient to transport portions of the charged reagent solution to each oppositely charged reagent electrode as reagent solution droplets, where each reagent solution droplet has a volume of 1 pL or less; and
discharge the reagent electrodes and the reagent solution droplets; and
when the reagent delivery chip is at the position over the synthesizer chip, the reagent delivery chip is further configured to:
electrically charge each reagent solution droplet in the at least a portion of the array of reagent delivery units with a third charge;
electrically charge each reaction electrode corresponding to a reagent delivery unit having a reagent solution droplet with a fourth charge having a charge polarity opposite to the third charge, where the fourth charge is sufficient to transport each charged reagent solution droplet to the corresponding oppositely charged reaction electrode; and discharge the charged reagent solution droplets.

15. The system of claim 14, wherein the reagent delivery chip is further configured to:

receive a reagent request for delivery to a portion of the array of reaction units;

instruct the transport controller to move the transporter with the reagent delivery chip to the position above the reagent solution tray;

fill a portion of the array of reagent delivery units corresponding to the portion of the array of reaction units with reagent solution droplets;

instruct the transport controller to move the transporter to the position over the synthesizer chip; and deliver the reagent solution droplets from the portion of the array of reagent delivery units to the corresponding portion of the array of reaction units.

16. The system of claim 15, further comprising:

a horizontal alignment sensor functionally coupled between the synthesizer chip and the reagent delivery chip configured to measure a horizontal planar misalignment between the array of reaction units and the array of reagent delivery units; and an alignment controller functionally coupled to the horizontal alignment sensor configured to;

receive the horizontal planar misalignment from the horizontal alignment sensor; and compare the horizontal planar misalignment to a misalignment threshold;

if the horizontal planar misalignment is greater than the misalignment threshold, the alignment controller is configured to instruct the transport controller to move the transporter in a direction to decrease the horizontal planar misalignment; and if the horizontal planar misalignment is less than or equal to the misalignment threshold, the alignment controller is configured to send an alignment acknowledgment to the control processor reagent delivery chip.

17. The system of claim 15, wherein the reagent request is for a different reagent, and the reagent delivery chip is further configured to:

instruct the transport controller to move the transporter with the reagent delivery chip to a different position above a different reagent solution tray;

fill a portion of the array of reagent delivery units corresponding to the portion of the array of reaction units with different reagent solution droplets;

instruct the transport controller to move the transporter to the position over the synthesizer chip; and deliver the different reagent solution droplets from the portion of the array of reagent delivery units to the corresponding portion of the array of reaction units.

18. The system of claim 13, where each reaction surface of the array of reaction units is positioned at a bottom of a reaction well in each reaction unit.

* * * * *